US010201398B2

United States Patent
Fisher et al.

(10) Patent No.: US 10,201,398 B2
(45) Date of Patent: Feb. 12, 2019

(54) DISPENSING MATERIAL FROM A DENTAL HANDPIECE

(71) Applicants: Kaltenbach & Voigt GmbH, Biberach (DE); KaVo Dental Technologies, LLC, Charlotte, NC (US); Kerr Corporation, Orange, CA (US)

(72) Inventors: Michael Aaron Fisher, Bala Cynwyd, PA (US); Robert Thomas St. Louis, Charlotte, NC (US); Gopikrishnan Soundararajan, Santa Clara, CA (US); Matteo Riccardo Bosisio, Lugano (CH); Michael Carl Dunaway, Charlotte, NC (US)

(73) Assignees: Kaltenbach & Voigt GmbH, Biberach (DE); KaVo Dental Technologies, LLC, Charlotte, NC (US); Kerr Corporation, Orange, CA (US)

( * ) Notice: Subject to any disclaimer, the term of this patent is extended or adjusted under 35 U.S.C. 154(b) by 138 days.

(21) Appl. No.: 15/074,893

(22) Filed: Mar. 18, 2016

(65) Prior Publication Data
US 2016/0270876 A1  Sep. 22, 2016

Related U.S. Application Data

(63) Continuation-in-part of application No. 14/663,607, filed on Mar. 20, 2015, now abandoned.

(51) Int. Cl.
*A61C 1/10* (2006.01)
*A61C 1/07* (2006.01)
(Continued)

(52) U.S. Cl.
CPC .............. *A61C 1/07* (2013.01); *A61C 1/0015* (2013.01); *A61C 1/087* (2013.01); *A61C 5/62* (2017.02); *A61C 17/20* (2013.01); *A61C 5/55* (2017.02)

(58) Field of Classification Search
CPC ......... A61C 5/062; A61C 5/068; A61C 5/064; A61C 9/026; B05C 17/01; B05C 17/0116; B05C 17/0123
See application file for complete search history.

(56) References Cited

U.S. PATENT DOCUMENTS

| 3,466,689 A | 9/1969 | Aurelio et al. |
| 3,513,550 A | 5/1970 | Ekman |

(Continued)

FOREIGN PATENT DOCUMENTS

| JP | 2006035149 | 2/2006 |
| JP | 2006038661 | 2/2006 |

(Continued)

OTHER PUBLICATIONS

PCT/US2016/023279 International Search Report and the Written Opinion of the International Searching Authority dated Aug. 25, 2016 (26 pages).

(Continued)

*Primary Examiner* — Nicholas Lucchesi
(74) *Attorney, Agent, or Firm* — Michael Best & Friedrich LLP

(57) ABSTRACT

Devices and methods for dispensing material from a dental handpiece. In one example, the method includes receiving an input that indicates that an amount of the material is to be dispensed from the container of the dental handpiece. The method also includes rotating an electric motor to rotate an imbalanced mass to vibrate a vibration transmission element that vibrates the material in the container. The method also (Continued)

includes dispensing the amount of the material from the container with a piston based on the input.

24 Claims, 20 Drawing Sheets

(51) Int. Cl.
*A61C 1/00* (2006.01)
*A61C 17/20* (2006.01)
*A61C 1/08* (2006.01)
*A61C 5/62* (2017.01)
*A61C 5/55* (2017.01)

(56) References Cited

U.S. PATENT DOCUMENTS

| | | | |
|---|---|---|---|
| 3,763,411 A | 10/1973 | Goof | |
| 3,919,775 A | 11/1975 | Malmin | |
| 3,924,335 A | 12/1975 | Balamuth et al. | |
| 4,025,809 A | 5/1977 | Teranishi | |
| 4,114,271 A | 9/1978 | Howa | |
| 4,278,428 A | 7/1981 | Straihammer et al. | |
| 4,330,282 A | 5/1982 | Nash | |
| 4,608,019 A | 8/1986 | Kumabe et al. | |
| 5,247,218 A | 9/1993 | Sven | |
| 5,343,883 A | 9/1994 | Murayama | |
| 5,431,565 A | 7/1995 | Euvrard | |
| 5,501,596 A | 3/1996 | Bailey | |
| 5,636,988 A | 6/1997 | Murayama | |
| RE36,699 E | 5/2000 | Murayama | |
| 6,631,829 B1 * | 10/2003 | Wagner | B05C 17/00506 222/23 |
| 6,716,028 B2 | 4/2004 | Rahman et al. | |
| 7,014,462 B1 | 3/2006 | Tilse | |
| 8,435,034 B2 | 5/2013 | Gersh et al. | |
| 2003/0020345 A1 | 1/2003 | Mooney | |
| 2003/0031979 A1 | 2/2003 | Shortt et al. | |
| 2003/0162146 A1 | 8/2003 | Shortt et al. | |
| 2005/0008986 A1 | 1/2005 | Sokol et al. | |
| 2005/0032017 A1 | 2/2005 | Levy | |
| 2005/0048436 A1 * | 3/2005 | Fishman | A61C 17/02 433/80 |
| 2005/0091770 A1 | 5/2005 | Mourad et al. | |
| 2005/0255427 A1 | 11/2005 | Shortt et al. | |
| 2006/0063130 A1 | 3/2006 | Hayman et al. | |
| 2006/0191086 A1 | 8/2006 | Mourad et al. | |
| 2006/0269901 A1 | 11/2006 | Rosenblood et al. | |
| 2007/0020580 A1 * | 1/2007 | Harre | A61C 5/60 433/89 |
| 2007/0190485 A1 | 8/2007 | Hayman et al. | |
| 2008/0014552 A1 | 1/2008 | Masterman et al. | |
| 2008/0057469 A1 * | 3/2008 | Hayman | A61C 1/07 433/118 |
| 2008/0144426 A1 * | 6/2008 | Janssen | B01F 7/00216 366/130 |
| 2008/0176183 A1 | 7/2008 | Gatzemeyer et al. | |
| 2008/0206706 A1 | 8/2008 | Mossle | |
| 2008/0209650 A1 | 9/2008 | Brewer et al. | |
| 2008/0318184 A1 | 12/2008 | Zargari et al. | |
| 2009/0023107 A1 | 1/2009 | Hayman et al. | |
| 2009/0202961 A1 | 8/2009 | Fani et al. | |
| 2010/0233646 A1 | 9/2010 | Brokx | |
| 2011/0041268 A1 | 2/2011 | Iwahori et al. | |
| 2011/0084097 A1 | 4/2011 | Guert | |
| 2011/0143303 A1 | 6/2011 | Kilcher et al. | |
| 2011/0159461 A1 | 6/2011 | Mourad et al. | |
| 2012/0028216 A1 | 2/2012 | Mossle | |
| 2012/0094251 A1 | 4/2012 | Mossle | |
| 2012/0141952 A1 | 6/2012 | Snyder et al. | |
| 2012/0202166 A1 | 8/2012 | Kilcher et al. | |
| 2012/0251975 A1 | 10/2012 | Iwahori | |
| 2013/0040267 A1 | 2/2013 | Bergheim et al. | |
| 2013/0198980 A1 | 8/2013 | Iwahori et al. | |
| 2014/0011163 A1 | 1/2014 | Montgomery | |
| 2014/0318287 A1 | 10/2014 | Eder et al. | |
| 2015/0147718 A1 | 5/2015 | Khakpour et al. | |
| 2015/0173852 A1 | 6/2015 | Khakpour et al. | |
| 2016/0056685 A1 | 2/2016 | Fujimoto et al. | |
| 2016/0067638 A1 | 3/2016 | Raddemacher | |
| 2016/0144404 A1 | 5/2016 | Houston et al. | |

FOREIGN PATENT DOCUMENTS

| | | |
|---|---|---|
| JP | 2008110217 | 5/2008 |
| WO | 2004073538 A2 | 9/2004 |

OTHER PUBLICATIONS

Office Action from the US Patent and Trademark Office for U.S. Appl. No. 14/663,607 dated Jul. 27, 2016 (16 pages).

Hiemstra et al., "Performance Tradeoffs Posed by Moving Magnet Actuators in Flexure-Based Nanopositioning"Transactions on Mechatronics, 2012, 12 pages.

* cited by examiner

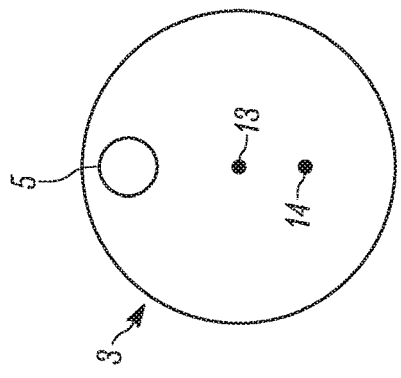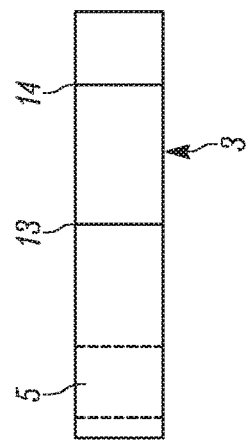
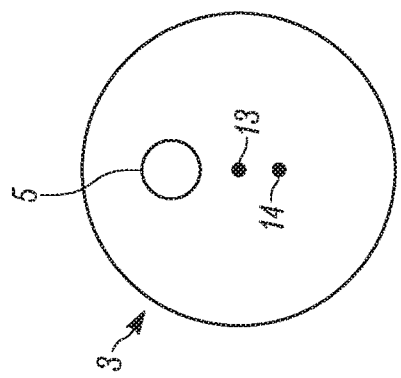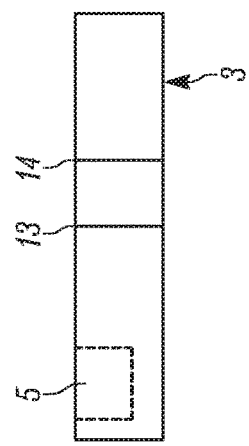
FIG. 2
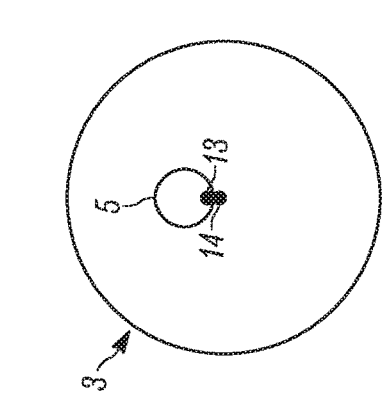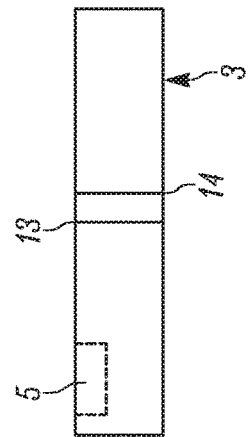
FIG. 3

DISPENSING MATERIAL FROM A DENTAL HANDPIECE

CROSS-REFERENCE TO RELATED APPLICATION

This application is a continuation-in-part of U.S. patent application Ser. No. 14/663,607, filed Mar. 20, 2015, the entire content of which is hereby incorporated by reference.

BACKGROUND

Certain embodiments relate to a vibration generator for generating mechanical vibrations for a dental handpiece, wherein the vibration generator comprises a rotation driving means, a vibration generating element and a vibration transmission element.

SUMMARY

Vibration generators for dental handpieces are currently used in both dental scalers and dental handpieces for delivering restoration composites.

Regarding the usage of vibration generators in dental scalers, it should be in general noted that in medical or dental medical technologies, a treatment of the human or animal body, or artificial parts thereof (prostheses) can be effected with a tool of a treatment instrument in various ways. In many cases, there is necessary merely a treatment of the body without alternation of its shape. Here, there may be involved, for example, a surface treatment in the manner of a massage. Another kind of treatment consists in altering the shape of the body, such as it is the case, for example, with a material removing working. This treatment instruments of the kind concerned, appropriately designed, the tool is set into oscillation respectively vibration by means of an oscillatory drive respectively vibration generator, wherein the frequency lies in particular in the sonic or ultrasonic range.

Regarding the usage of vibration generators in dental handpieces for delivering restoration composites, it should be noted that in general in medical technology it is known to fill, and therefore to repair, cavities in an animal or human body part or in a prosthesis with a filler material, for example, after grinding or cutting away, or otherwise mechanically removing a defect. For this, curable filler masses are used, which are brought into the cavity in a pasty or liquid condition and then harden. Currently, for example, dental masses are used, which contain a binder or such a high proportion of filler materials that the dental mass itself is difficult to use for the intended purpose due to its high viscosity. However, by supplying oscillation energy respectively vibration energy, the viscosity of for example a pasty filler mass can be reduced to a more easily usable value.

In both areas, there exist dental scalers as well as dental handpieces for delivering restoration composites, having different kinds of oscillation drives or vibration generators. On the one hand, some devices comprise a piezo function, which generates a vibration in the sonic or ultrasonic range. On the other hand, other devices are known which comprise a pneumatic function that again generates a vibration in the sonic or ultrasonic range.

Two different kinds of generating a vibration are shown in DE 100 39 198 A1 and DE 10 2005 028 925 A1, wherein in these documents on the one side, a dental scaler and on the other side a dental handpiece for delivering restoration composites is shown. Further examples of dental scalers and dental handpieces for delivering restoration composites include the SONICflex and SONICfill products of the applicant Kaltenbach & Voigt GmbH.

Each kind of generating a vibration has different disadvantages. For example, it is not possible to adjust the frequency and amplitude independently from each other when using a conventional pneumatic device. Another drawback is that in pneumatic devices the output air must be exhausted. Thereby, the exhaust port must be designed to avoid directing the pressurized air into the patient's open tooth/root as the air can cause discomfort and/or contaminate the tooth.

It is therefore an object of certain embodiments to propose an alternative generator for generating vibrations for a dental handpiece.

Some embodiments relate to a vibration generator for generating mechanical vibrations for a dental handpiece, which comprises a rotation driving means, a vibration generating element and a vibration transmission element. The vibration generating element is rotationally coupled to the rotation driving means and comprises an imbalanced vibrating portion. The vibration transmission element is in mechanical communication with the vibration generating element. Further, the rotation of the vibration generating element causes the imbalanced vibrating portion to generate vibrations of the vibration transmission element, wherein the vibration transmission element is configured to deliver the vibrations to an object.

Certain embodiments, therefore, provide a new solution for generating mechanical vibrations for a dental handpiece.

The imbalanced vibrating portion can be an imbalanced flywheel, wherein the imbalanced flywheel in particular can be formed by a disk comprising at least one imbalancing hole or opening, the imbalancing hole or opening being offset from an axis of rotation of the vibration generating element.

Further, the imbalanced vibrating portion can comprise a shape having at least one cut-away portion, the cut-away portion being offset from an axis of rotation of the vibration generating element.

Advantageously, the vibration generator can further comprise at least one speed-increasing gear provided between the rotation driving means and the vibration generating element, wherein the at least one speed-increasing gear in particular comprises a gear train of at least two consecutive speed-increasing gears provided between the rotation driving means and the vibration generating element.

In addition, the vibration generator can comprise a second vibration generating element in mechanical communication with the vibration transmission element, wherein the rotation of the second vibration generating element generates vibration of the vibration transmission element. Thereby, the rotational speeds of the two vibration generating elements can be the same and the vibration generator can further comprise means for adjusting a phase between rotational movements of the two vibration generating elements.

The vibration generator can also comprise a second vibration generating element rotationally coupled to a driving shaft of the rotation driving means, wherein the vibration transmission element supports the first and second vibration generating elements and the vibration generator further comprises means for adjusting a phase of the rotational movement of the two vibration generating elements.

Thereby, the means for adjusting a phase of the rotational movement of the two vibration generating elements comprise a gear train transferring a rotation of the drive shaft to one of the two vibration generating elements, wherein the gear train comprises a phase-adjustment gear portion and the phase-adjustment gear portion in particular comprises a bevel gear arrangement, wherein one beveled gear wheel of the bevel gear arrangement is displaceable around a longitudinal axis of the gear train to adjust a phase of rotation of the corresponding vibration generating element.

The rotation driving means can comprise a motor, in particular an electric motor.

Further, the vibrations can have a displacement amplitude between 5 micrometers and 500 micrometers. Preferably, the vibrations have a displacement amplitude between 50 micrometers and 200 micrometers. Further preferably, the vibrations have a displacement amplitude of approximately 100 micrometers.

The object can also comprise a container containing a substance having a physical property that changes under vibration, wherein the physical property in particular comprises a viscosity, and the object further comprises a tip for providing the substance, for example to a tooth.

The object can comprise a vibratable treatment instrument, in particular a scaler tip, and a body part in a patient's oral cavity, wherein the body part in particular comprises a tooth.

Other embodiments provide a dental handpiece for dispensing a pasty filler mass, the viscosity of which can be used by supplying vibration energy, wherein the handpiece has a handpiece housing, means for holding a container for the pasty filler mass and a vibration generator and the vibration generator is a generator according to one of the above-described.

Alternatively, the some embodiments provide a dental handpiece comprising an elongated gripping sleeve, a vibratable treatment instrument, in particular a scaler tip, arranged at one end of the gripping sleeve and a vibration generator arranged in the gripping sleeve to generate vibrations, wherein the vibration generator is a generator according to one of the above-described. This handpiece can be a dental scaler.

The present invention further relates to a method for manufacturing a dental handpiece, comprising the steps of providing a rotation driving means, imbalancing an object to form an imbalanced vibrating portion, providing a vibration generating element rotationally coupled to the rotation driving means and comprising the imbalanced vibrating portion and providing a vibration transmission element in mechanical communication with vibration generating element, wherein the rotation of the vibration generating element causes the imbalanced vibrating portion to generate vibrations of the vibration transmission element and the vibration transmission element is configured to deliver the vibrations to an object.

As mentioned above, the present invention can be an alternative to a pneumatic vibration generator or a piezo vibration generator, wherein the vibration generator of the present invention generates mechanical vibrations for a dental handpiece by using, for example, an imbalanced flywheel, which is for example driven by an electric motor. The imbalanced flywheel then generates vibrations of a vibration transmission element, wherein the vibrations are then delivered by the vibration transmission element to an object as a tooth or a container containing a substance.

In one embodiment, the invention provides a dental handpiece comprising a power source, a controller, a vibration generator, a linear electromagnetic actuator, a magnet, a container, a vibration transmission element, and a tip. The controller is electrically connected to the power source. The vibration generator is configured to generate vibrations by rotating an imbalanced mass, the vibration generator having an electric motor electrically connected to the controller. The linear electromagnetic actuator electrically connected to the controller. The container configured to hold a material and having a piston. The vibration transmission element configured to transmit vibrations caused by rotation of the imbalanced mass to the container. The linear electromagnetic actuator is configured to move the piston of the container to dispense the material through the tip while the container is vibrated by the vibration transmission element.

In another embodiment, the invention provides a method for dispensing a material within a container of a dental handpiece. The method includes receiving an input that indicates that an amount of the material is to be dispensed from the container of the dental handpiece. The method includes rotating an electric motor to rotate an imbalanced mass to vibrate a vibration transmission element that vibrates the material in the container. The method also includes dispensing the amount of the material from the container with a piston based on the input.

In yet another embodiment, the invention provides a dental handpiece comprising a squeeze handle, a vibration generator, a container, a vibration transmission element, and a tip. The squeeze handle mechanically linked to a pushrod. The vibration generator configured to generate vibrations by rotating an imbalanced mass, the vibration generator having an electric motor. The container configured to hold a material and having a piston. The vibration transmission element configured to transmit vibrations caused by rotation of the imbalanced mass to the material of the container. The squeeze handle and the pushrod are configured to move the piston of the container to dispense the material through the tip while the container is vibrated.

In another embodiment, the invention provides a dental handpiece comprising a power source, a controller, a vibration generator, a linear electromagnetic actuator, a magnet, a container, and a tip. The controller electrically connected to the power source. The vibration generator having a plurality of stator coils that are configured to generate a rotating magnetic field, and a member that is configured to vibrate in response to the rotating magnetic field. The linear electromagnetic actuator electrically connected to the controller. The container configured to hold a material and having a piston. The container is also configured to receive vibrations transmitted by the member. The linear electromagnetic actuator is also configured to move the piston of the container to dispense the material through the tip while the container receives the vibrations transmitted by the member.

These and other aspects and advantages of embodiments will become more apparent when studying the following detailed description, in connection with the figures.

BRIEF DESCRIPTION OF THE DRAWINGS

FIG. 2 shows three different imbalanced flywheels in a top view.

FIG. 3 shows three different imbalanced flywheels in a side view.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The dental handpieces shown in the FIGS. 1a and 4-8 can be used for delivering restoration composites, for example, for dispensing a pasty filler mass, whose viscosity can be reduced by supplying vibration energy. Each dental handpiece shown in the FIGS. 1a and 4-8 comprises a handpiece housing, a container containing the pasty filler mass, means for holding the container and a vibration generator, wherein the vibrations of the vibration generator are delivered to the container and a tip for providing the pasty filler mass, for example, to a tooth.

As already described above, some embodiments provide an alternative solution for generating oscillations respectively vibrations for a dental handpiece. Therefore, the vibration generator of the present invention can be used not only for a dental handpiece for delivering restoration composites, but also for dental scalers, as it is shown in FIG. 1b. In this case, a dental handpiece would then comprise an elongated gripping sleeve, a vibratable treatment instrument, in particular a scaler tip, arranged at one end of the gripping sleeve and the vibration generator arranged in the gripping sleeve to generate vibrations, wherein the vibrations are then delivered to the vibratable treatment instrument and a body part in a patient's oral cavity. The body part in a patient's oral cavity can be for example a tooth. Preferably, the vibrations have an amplitude large enough to clean or scale the tooth, but small enough to avoid damaging the tooth.

In view of the already mentioned products of the applicant Kaltenbach & Voigt GmbH, it should be noted that in the following the dental handpieces in the FIGS. 1a and 4-8 are described regarding the SONICfill products. In addition, a vibration generator of the present invention can of course also be used in the SONICflex products as in FIG. 1b.

The currently known devices for generating a vibration have, as cited above, different disadvantages. Therefore, some embodiments provide an alternative solution of a vibration generator for generating mechanical vibrations for a dental handpiece.

Figure 1A:
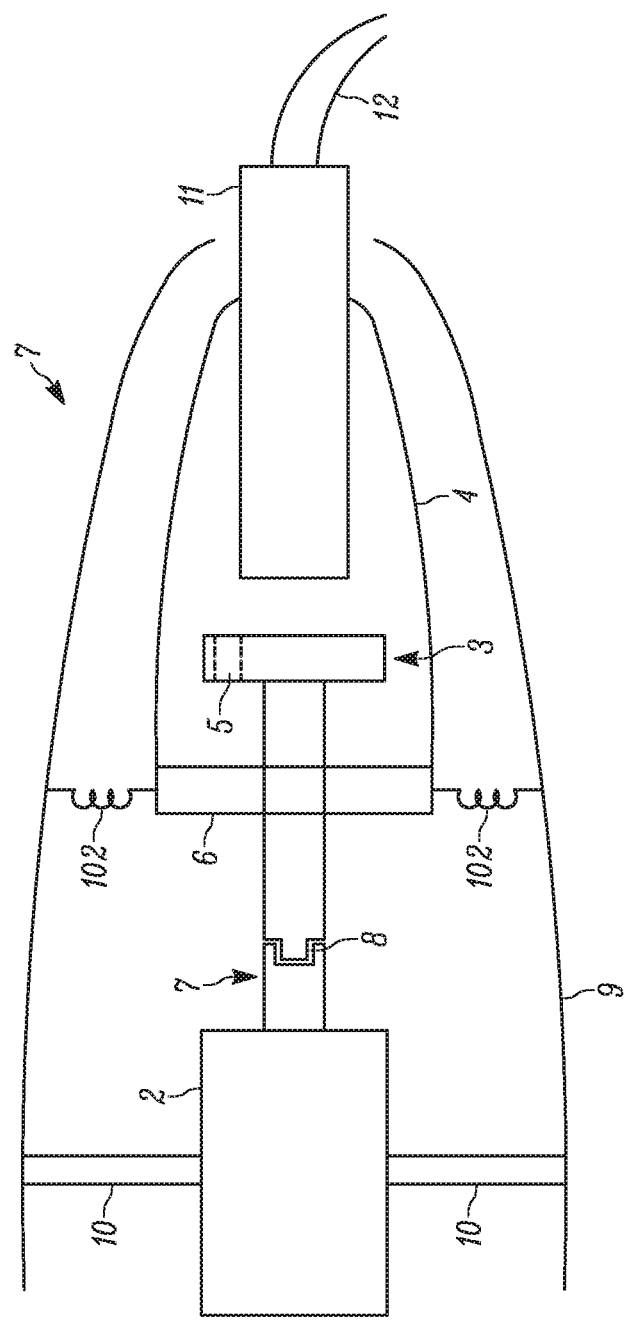
FIG. 1a shows a dental handpiece for dispensing a pasty filler mass comprising a vibration generator.
Figure 1B:
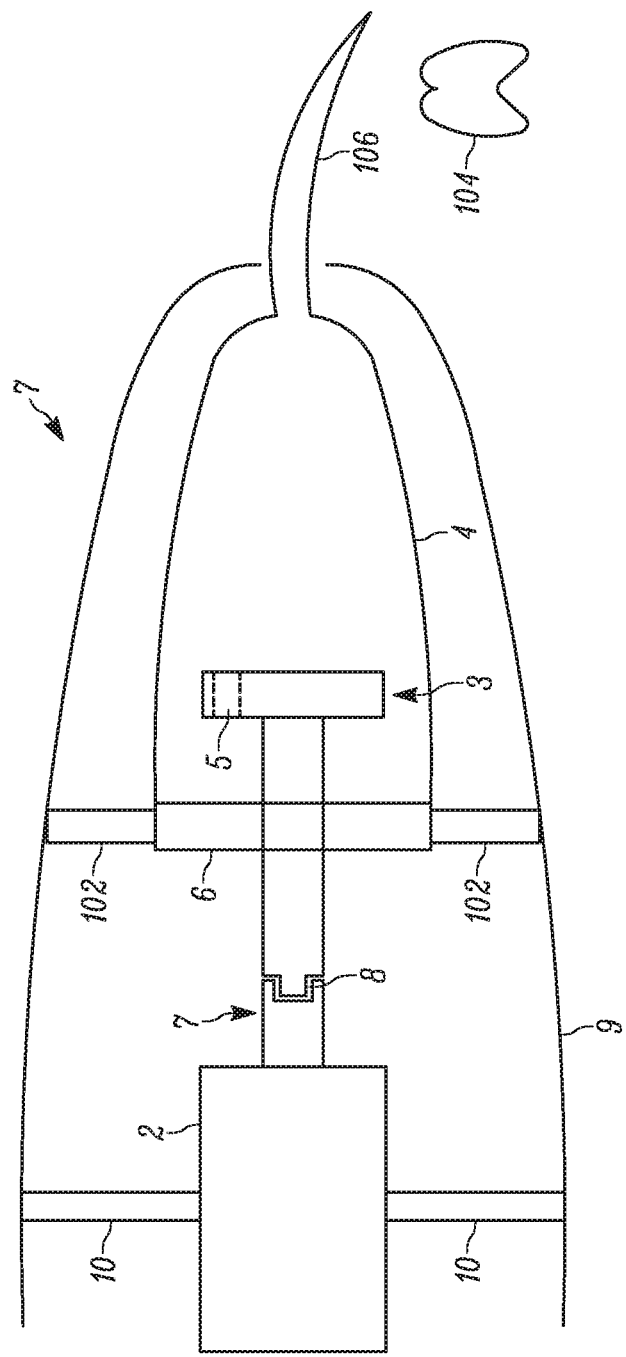
FIG. 1b shows a dental scaler comprising a vibration generator.

FIG. 1a shows a dental handpiece 1 with a vibration generator. The vibration generator comprises a rotation driving means 2, a vibration generating element and a vibration transmission element 4. The vibration generating element is rotationally coupled to the rotation driving means 2 and comprises an imbalanced vibrating portion 3 and the vibration transmission element 4 is in mechanical communication with the vibration generating element, wherein the rotation of the vibration generating element causes the imbalanced vibrating portion 3 to generate vibrations of the vibration transmission element 4 and the vibration transmission element 4 is configured to deliver the vibrations to an object 11, 12.

In FIG. 1a the rotation driving means is a motor 2, in particular a DC or AC electric motor, which spins the vibration generating element and thus the imbalanced vibrating portion, which is in FIG. 1a an imbalanced flywheel 3 and is in particular formed by a disk. The imbalanced disk or flywheel 3 then comprises at least one imbalancing hole or opening 5, wherein this imbalancing hole or opening 5 is offset from an axis of rotation of the vibration generating element, wherein this off-center hole or opening 5 can be, for example drilled in an easy and simple way in the imbalanced disk or flywheel 3.

The vibration transmission element, which in FIG. 1a is an inner vibration transmitting member 4, is positioned in the dental handpiece 1 inside a handpiece housing respectively outer case 9, which surrounds the motor 2, all the parts of the vibration generating element and the vibration transmission element 4.

In the example illustrated in FIG. 1a, the imbalanced flywheel 3 is positioned inside the vibration transmission element 4 so that the rotation of the vibration generating element by the motor 2 causes the imbalanced flywheel 3 to generate vibrations of the vibration transmission element 4. But optionally, the imbalanced flywheel 3 can be also positioned outside the vibration transmission element 4. Further the vibration transmission element 4 in FIG. 1a partly covers a container 11 containing for example restoration composites, wherein the container 11 is connected with a tip 12 for providing the restoration composites, for example to a tooth. But optionally, the vibration transmission element 4 does not need to cover any part of the container 11. The container 11 could be for example a SONICfill capsule of the applicant and can then be further connected to a so-called SONICfill tip as a tip 12 for providing the restoration composites, for example to a tooth.

The container 11 is now positioned in such a way and arranged in view of the vibration transmission element 4 that the vibration transmission element 4 can deliver the vibrations to the container 11. As mentioned above, the container 11 can contain a substance having a physical property that changes under vibration, for example a restoration composite for teeth, wherein the physical property in particular comprises a viscosity. For example, the restoration composite can comprise a thixotropic material.

In the example illustrated in FIG. 1a, the vibration transmission element 4 is affixed to the outer case/housing 9 through one or more compliant mounts 102 to keep the vibration transmission element 4 positioned within the outer case 9 while allowing the vibration transmission element 4 to vibrate. In FIG. 1a, the compliant mounts are illustrated schematically as one or more springs 102, but optionally they can comprise any compliant structure, for example, a rubber or polymer O-ring or one or more members formed from any other compliant material.

In FIG. 1a it can be further seen that the motor 2, which spins the vibration generating element and, thus, the imbalanced flywheel 3, is mounted in the outer case 9 by motor mounts 10. In addition, the imbalanced flywheel 3 is coupled to the motor 2 via a driving shaft 7, which optionally comprises a rotational coupler 8. The imbalanced flywheel 3 is, therefore, rotationally coupled to the motor 2. To keep the driving shaft 7 in position, the dental handpiece 1 in FIG. 1a further comprises a bearing 6.

As already mentioned above, FIG. 1b shows a dental handpiece 1 with a vibration generator, wherein the dental handpiece 1 is a dental scaler. Similar to the dental handpiece 1 in FIG. 1a, the dental handpiece 1 in FIG. 1b also comprises a motor 2, an imbalanced flywheel 3 with an imbalancing hole or opening 5, a vibration transmission element 4, a bearing 6, a driving shaft 7, a rotational coupler 8, an outer case 9, motor mounts 10 and compliant mounts 102. In contrast to the dental handpiece 1 in FIG. 1a, the dental handpiece 1 in FIG. 1b does not comprise a container and a tip for providing restoration composites. Instead, a scaler tip 106 as a vibratable treatment instrument is provided, which is in contact with the vibration transmission element 4, so that the vibrations of the vibration transmission element 4 can be delivered to the scaler tip 106 and further to a tooth 104 as a body part in a patient's oral cavity to clean or scale the tooth 104.

FIG. 2 shows three different imbalanced flywheels 3, wherein the distance between the imbalancing hole 5 causing the imbalance and the axis of rotation respectively center of rotation 13 of the imbalanced flywheel 3 differs from one to the other imbalanced flywheel 3. Here, it should be noted that the distance between the hole 5 and the center of rotation 13 determines the center of mass 14 of the imbalanced flywheel 3 and, thus, determines the amount of imbalance.

As mentioned above, in FIG. 2 the three imbalanced flywheels 3 have each a different distance between the hole 5 and the center of rotation 13, wherein the imbalanced flywheel 3 on the left side of FIG. 2 has the biggest distance, the imbalanced flywheel 3 on the right side of FIG. 2 has the smallest distance and the imbalanced flywheel 3 in the middle of FIG. 2 has a medium distance. Therefore, the imbalanced flywheel 3 on the left side has a strong imbalance, the imbalanced flywheel 3 in the middle has a moderate imbalance and the imbalanced flywheel 3 on the right side has a weak imbalance. By changing the imbalance of the imbalanced flywheel 3, it is possible to change the amplitude of the vibrations, wherein, at a given angular velocity, a greater imbalance will produce higher-amplitude vibrations. Preferably, the amount of imbalance is selected such that, at the normal operating speed of the imbalanced flywheel 3, the amplitude of the vibrations is sufficient to reduce the viscosity of the restoration composite to a level at which the composite is easy work with, yet the vibrations are not so strong as to cause discomfort to the patient.

For example, a vibration displacement amplitude of approximately 100 μm (microns or micrometers) at a frequency of 6 kHz is optimal for some restoration composites. This can be expressed in terms of velocity amplitude—for example restoration composites have been known to work at a velocity amplitude of about 600 mm/s. However, the invention is not limited to these specific amplitudes. For example, some composites can exhibit a noticeable thixotropic effect with vibration amplitudes as low as 50 μm, 5 μm, or even lower. Furthermore, a useful handpiece can generate vibration amplitudes as large as 200 μm, 500 μm, or even more. Thus, in some exemplary cases the optimal vibration amplitude(s) can be within the range of 5-500 μm, or within the range of 50-200 μm. However, higher or lower amplitudes are also contemplated to be within the present inventive concept.

An alternative solution to change the imbalance of the imbalanced flywheel 3 is shown in FIG. 3. There, again three different imbalanced flywheels 3 are shown, however, the distance between the imbalancing hole 5 and the center of rotation 13 is always the same. To change the amount of imbalance, the depth of the hole 5 is now changed or adjusted, as it is shown in FIG. 3. As can be seen from FIG. 3, a higher depth of the hole 5 causes that the center of mass 14 is more far away from the center of rotation 13 and thus a higher or stronger imbalance is the result. This is shown in detail in the imbalanced flywheel 3 on the left side of FIG. 3. In contrast thereto, a smaller depth of the hole 5 causes, as shown on the right side of FIG. 3, that the center of mass 14 is closer to the center of rotation 13 and thus a weaker imbalance is the result. The imbalanced flywheel 3 in the middle of FIG. 3 shows a medium or moderate depth of the hole 5, which causes a moderate imbalance.

In FIGS. 2 and 3 two different possibilities are shown to change or adjust the amount of imbalance of the imbalanced flywheel 3. It should be noted that both possibilities, changing the distance between the hole 5 and the center of rotation 13 and changing the depth of the hole 5, could also be combined in that, for example, at the same time the distance is changed and also the depth of the hole 5. Further, also other solutions for changing or adjusting the amount of imbalance are possible for the imbalanced flywheel 3. In addition, the imbalanced vibrating portion mentioned in the present invention must not necessarily be an imbalanced flywheel. The imbalanced vibrating portion could comprise a shape having at least one cut-away portion, wherein the cut-away portion is offset from an axis of rotation of the vibration generating element.

Figure 4:
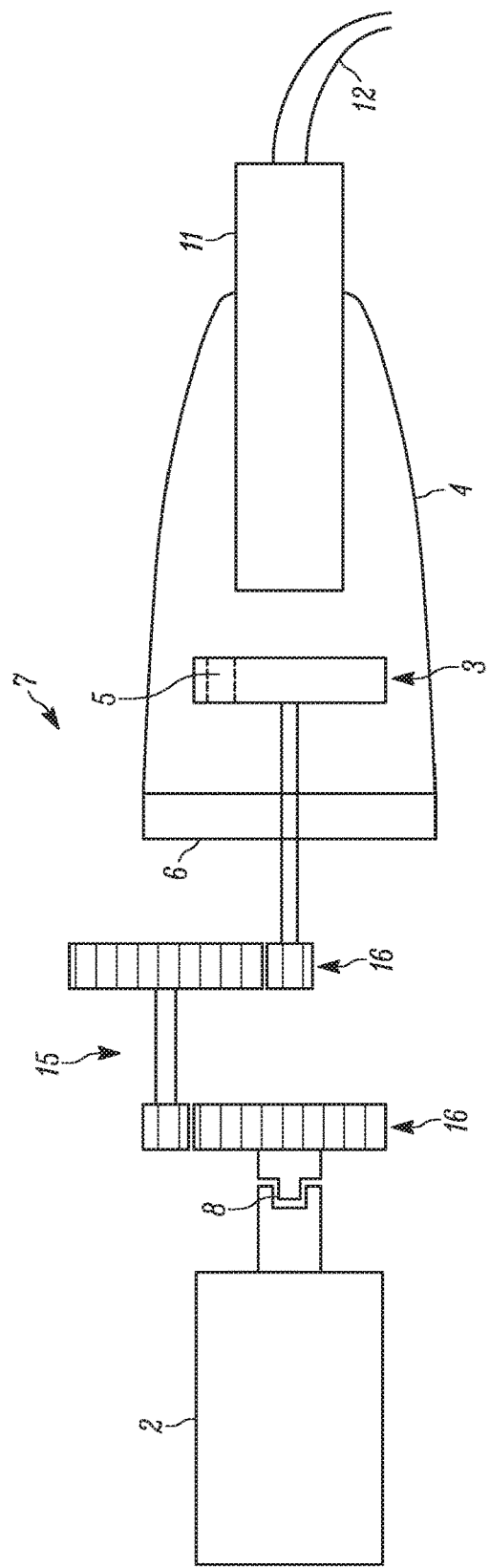
FIG. 4 shows a dental handpiece for dispensing a pasty filler mass comprising a vibration generator.

FIG. 4 shows a further dental handpiece 1, which is similar in some respects to the dental handpiece 1 in FIG. 1a and comprises some similar parts as the dental handpiece 1 in FIG. 1a. In addition, however, the vibration generator of the dental handpiece 1 in FIG. 4 now further comprises a speed-increasing gear 15, which is positioned between the motor 2 and the vibration generating element respectively the imbalanced flywheel 3.

The speed-increasing gear 15 is used in the vibration generator of the dental handpiece 1 of FIG. 4, since the substances contained in the container 11, as for example a restoration composite, currently often operates at a vibrational frequency of about 6 kHz, such as the SONICfill products. That means that the viscosity of the substance is in particular reduced by supplying vibration energy at a vibrational frequency of about 6 kHz. To match this frequency with a direct-drive device, such as illustrated in FIG. 1a, a motor would be required that spins at 6 kHz or 360.000 rpm. However, most of the dental motors currently used cannot exceed 30.000-40.000 rpm. To offer the possibility of still using a normal dental motor, the speed-increasing gear 15 is provided between the motor 2 and the imbalanced flywheel 3. The speed-increasing gear 15 in FIG. 4 thereby comprises a gear train of two consecutive speed-increasing gears 16. This is due to the fact that with the common dental motors with 30.000-40.000 rpm a 9:1 speed-increasing gear train is necessary to get a frequency of 6 kHz. In the vibration generator of the dental handpiece 1 in FIG. 4, the speed-increasing gear 15 comprises a gear train of two consecutive 3:1 speed increasing gears 16 by which a total speed increase of 9:1 is achieved.

However, although the current formulation of the SON-ICfill composite is optimized for use at 6 kHz, it is possible to formulate composites that exhibit substantial thixotropic properties at substantially higher or lower frequencies, as will be understood by those skilled in the art. For example, a composite that works sufficiently well at 600 Hz would not require the inclusion of the speed increasing gear 15 in the dental handpiece 1, because a direct drive with a 36.000 rpm motor 2 would suffice.

It should be noted that such a the speed-increasing gear 15 could be also applied to a dental handpiece 1 which is a dental scaler as shown in FIG. 1b, even though the dental handpiece 1 in FIG. 1b does not comprise a container with restoration composites.

In the vibration generators of the dental handpieces 1 of the FIGS. 1a, 1b and 4, it is possible to change or adjust the amplitude of the vibration by changing or adjusting the imbalance of the imbalanced flywheel 3, as described above. Additionally the amplitude of the vibration could be also changed or adjusted by changing the speed of the motor 2. However, this will also change the frequency, which may not always be desirable, depending on the frequency response of the viscosity of the restoration composite.

Figure 5:
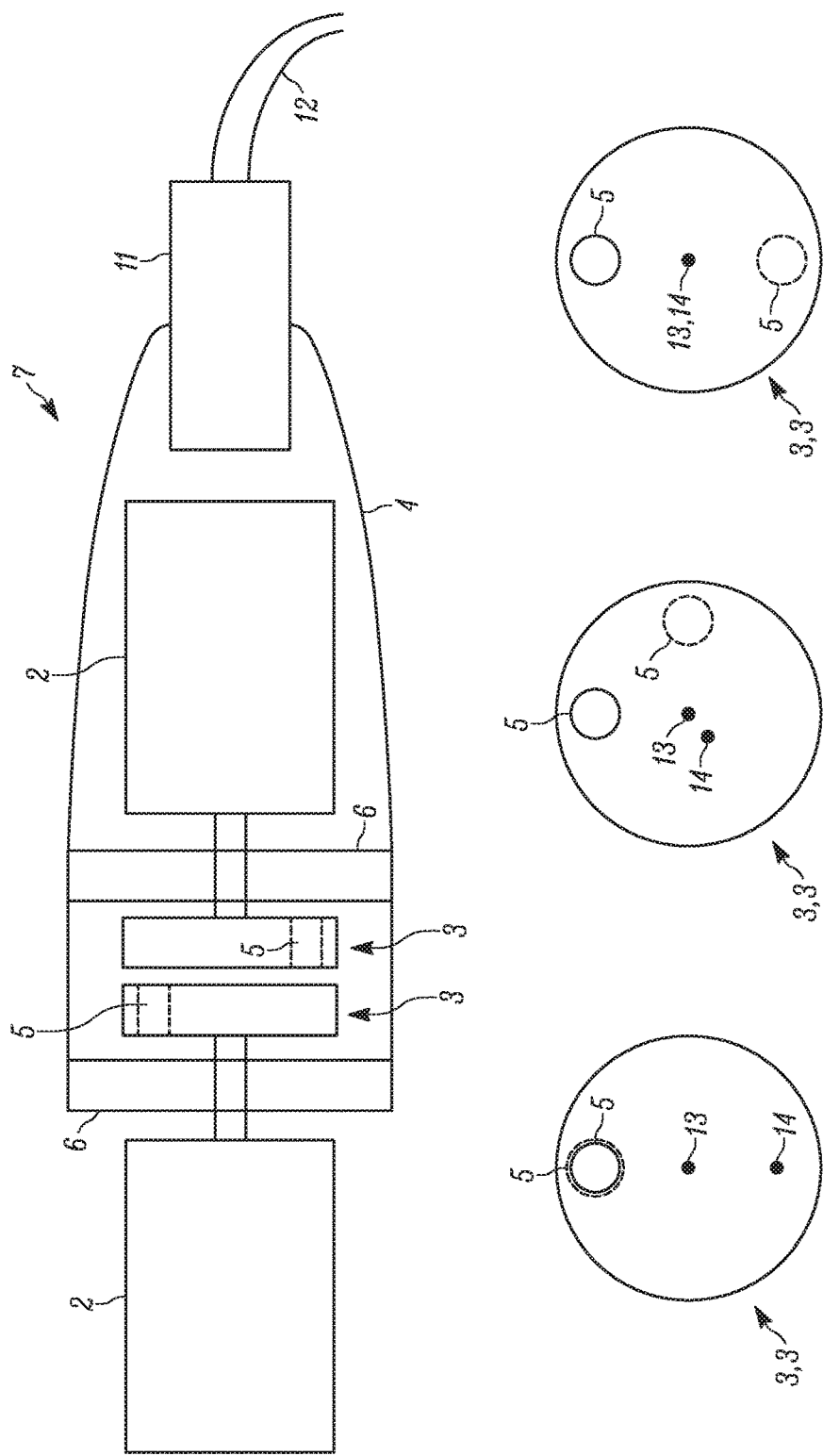
FIG. 5 shows a dental handpiece for dispensing a pasty filler mass comprising a vibration generator and the combination of a first imbalanced flywheel with a second imbalanced flywheel.

The vibration generator of the dental handpiece 1 shown in the top of FIG. 5 therefore has two vibration generating elements, a first one and a second one, wherein each vibration generating element comprises an imbalanced flywheel 3 and is in mechanical communication with the vibration transmission element 4. It should be noted that the dental handpiece 1 shown in the top of FIG. 5 comprises a couple of similar parts as the dental handpieces 1 in the FIGS. 1a, 1b and 4.

The first and second imbalanced flywheels 3 in the top of FIG. 5 correspond to the imbalanced flywheel 3 in the FIGS. 1a, 1b and 4 and thus, similar as in view of the imbalanced flywheel 3 in the FIGS. 1a, 1b and 4, also the rotation of the first and second imbalanced flywheels 3 in FIG. 5 generate vibrations of the vibration transmission element 4. As can be seen from the top of FIG. 5, the second imbalanced flywheel 3 is rotationally coupled to a second motor 2 and similar as in the FIGS. 1a and 1b the first imbalanced flywheel 3 is rotationally coupled to a first motor 2. That means that the first vibration generating element is rotationally coupled to the first rotation driving means 2 and comprises a first imbalanced vibrating portion 3 and the second vibration generating element is rotationally coupled to the second rotation driving means 2 and comprises a second imbalanced vibrating portion 3 and the vibration transmission element 4 is in mechanical communication with the first vibration generating element and with the second vibration generating element and the rotation of the first vibration generating element causes the first imbalanced vibrating portion 3 to generate vibrations of the vibration transmission element 4 and the rotation of the second vibration generating element causes the second imbalanced vibrating portion 3 to generate vibrations of the vibration transmission element 4.

With the use of two imbalanced flywheels 3 instead of one, which are spun by two different motors 2, it is now possible to adjust the amplitude of the vibration while keeping the frequency constant. The change or adjustment of the amplitude of the vibration by keeping the frequency constant is thereby achieved in that the rotational speeds of the two vibration generating elements and therefore of the two imbalanced flywheels 3 are the same and the vibration generator further comprises means for adjusting a phase between rotational movements of the two vibration generating elements respectively the two imbalanced flywheels 3.

This could be for example achieved if the two motors 2 are independently driven and the motors 2 are AC motors by which the relative phase of rotation of the two imbalanced flywheels 3 can be changed. Since the rotor of an AC motor 2 is phase-locked to the AC voltage driving it, the rotational phase of each motor 2—and thus the rotational phase of each imbalanced flywheel 3—can be controlled by controlling the phase of the AC drive voltage of each motor 2.

As shown in the bottom part of FIG. 5, the maximum vibration is obtained by rotating the two imbalanced flywheels 3 in-phase, thus causing a strong imbalance. This is illustrated on the left side of the bottom part of FIG. 5, where the two imbalanced flywheels 3 are shown in-phase so that the holes 5 of the two imbalanced flywheels 3 are lying upon each other and the center of mass 14 of both imbalanced flying wheels is far away of the center of rotation 13 of both imbalanced flywheels 3.

On the other hand, zero vibration can be obtained by rotating the imbalanced flywheels 3 180° out of phase, thus causing a balanced state without any imbalance. This is illustrated on the right side of the bottom part of FIG. 5, where the holes are shifted by 180° and thus the center of mass 14 of both imbalanced flywheels 3 in combination corresponds to the center of rotation 13 of both imbalanced flywheels 3.

An intermediate-amplitude vibration is obtained, for example, by rotating the imbalanced flywheels 3 90° (or any other angle between 0° and 180°) out of phase, as shown in the middle of the bottom part of FIG. 5 where the holes 5 are shifted by 90° and thus the center of mass 14 of both imbalanced flywheels is out of the center of rotation 13 of both imbalanced flywheels 3 but not as far as on the left side of the bottom part of FIG. 5.

Preferably the two vibration generating elements in FIG. 5 have identical imbalanced vibrating portions and thus identical imbalanced flywheels 3.

It should be mentioned that in the exemplary vibration generator of the dental handpiece 1 of FIG. 5, both imbalanced flywheels 3 are directly driven by the motors 2, in which case a simple design choice would be to place the motor 2 of the second imbalanced flywheel 3 towards the distal end of the handpiece. However, it is also possible to place both motors 2 on the coupler end of the dental handpiece 1 and convey the rotation using gears. In addition, it would also be possible to provide any kind of speed-increasing gear 15, for example the one shown in FIG. 4, between the first motor 2 and the first imbalanced flywheel 3 as well as between the second motor 2 and the second imbalanced flywheel 3.

The above-described adjustment of the amplitude of the vibration in the vibration generator of the dental handpiece 1 shown in FIG. 5 is an amplitude adjustment using varying electric phases. Alternatively or in addition, a mechanical amplitude adjustment using a phase-adjustment gear would also be possible.

Figure 6:
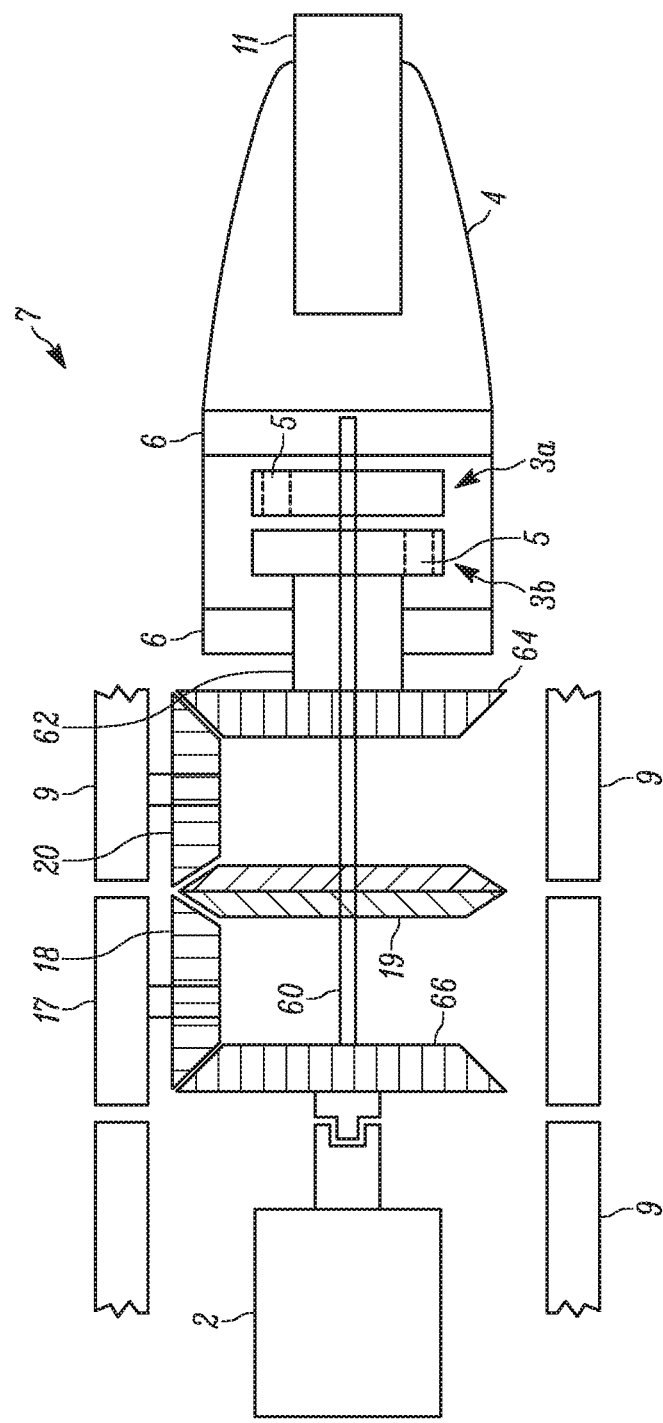
FIG. 6 shows a dental handpiece for dispensing a pasty filler mass comprising a vibration generator.
Figure 7:
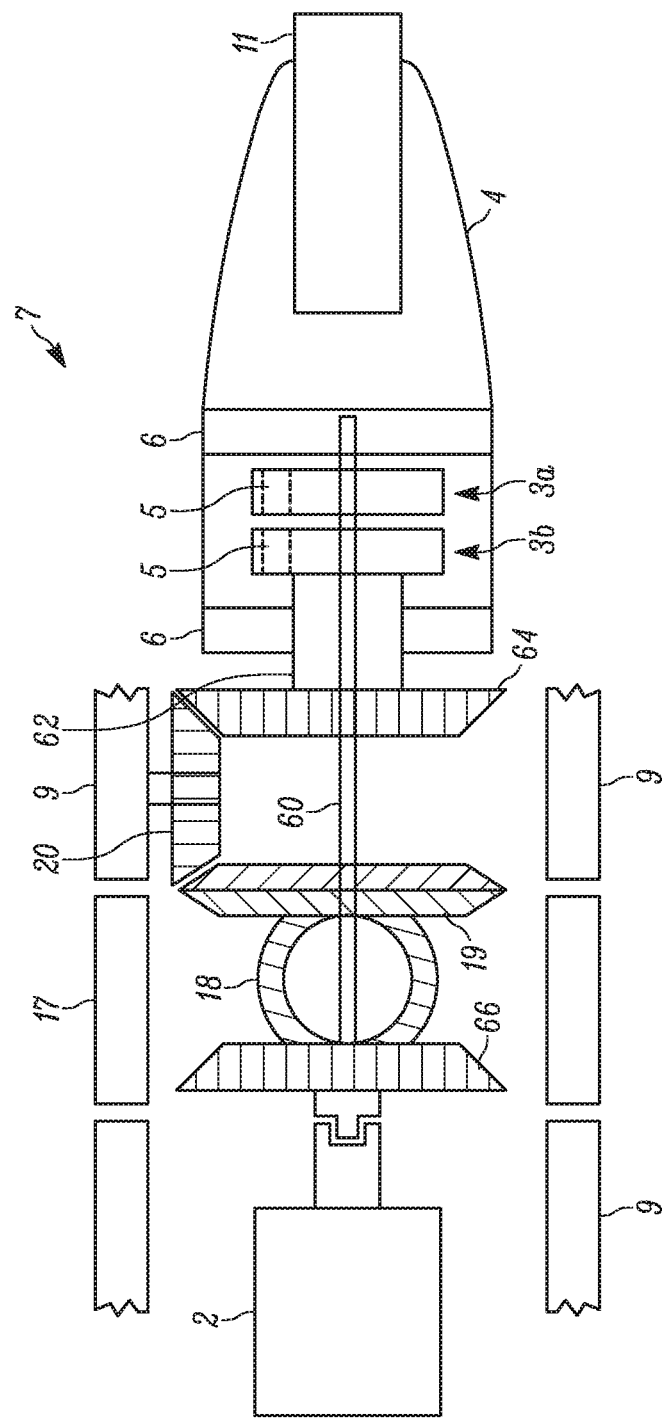
FIG. 7 shows a dental handpiece for dispensing a pasty filler mass comprising a vibration generator.
Figure 8:
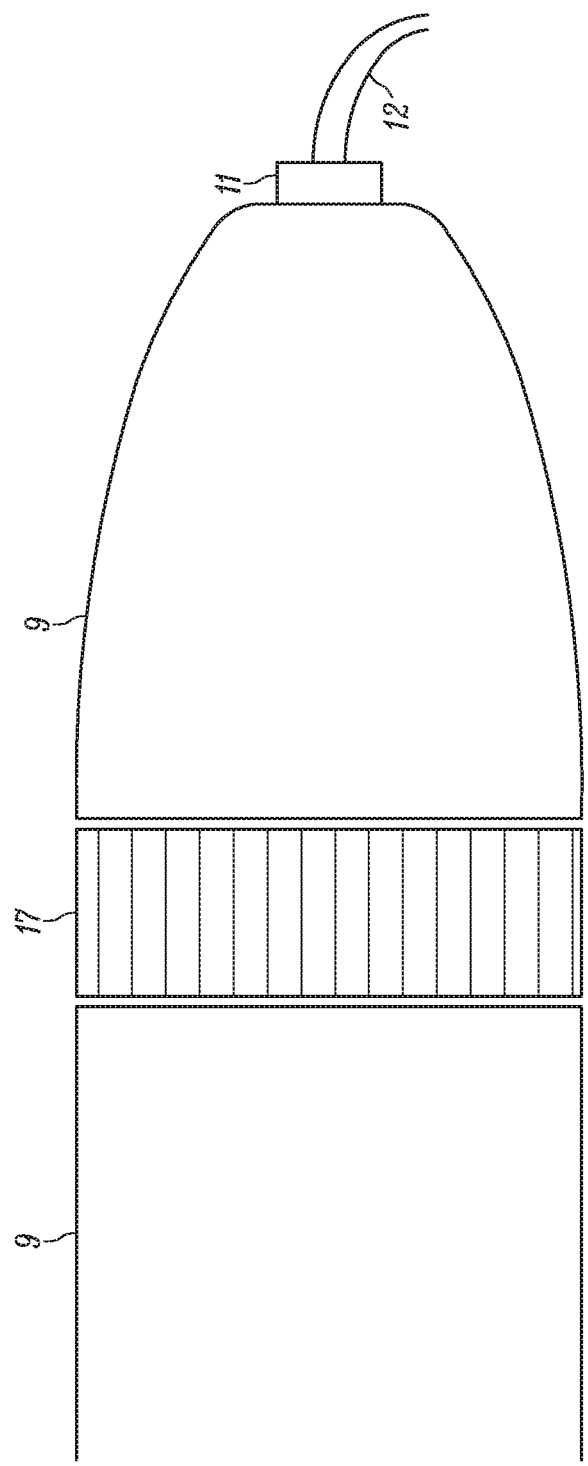
FIG. 8 shows a dental handpiece for dispensing a pasty filler mass comprising a vibration generator.

A corresponding dental piece 1 with a vibration generator that uses an exemplary mechanical amplitude adjustment is shown in the FIGS. 6, 7 and 8. It should be noted that the dental handpiece 1 shown in the FIGS. 6, 7 and 8 comprises some parts similar to those of the dental handpieces 1 in FIGS. 1*a*, 1*b* and 4.

Again, similarly to FIG. 5, in the FIGS. 6, 7 and 8 the vibration generator comprises a first vibration generating element and second vibration generating element, with a first imbalanced flywheel 3*a* rotationally coupled to the motor 2 through a first drive shaft 60, and a second imbalanced flywheel 3*b* rotationally coupled to the motor 2 through an initial bevel gear 66, a phase adjustment gear portion 18, a transmission gear 19, a direction-reversal gear 20, a final bevel gear 64, and a hollow drive shaft 62. In the illustrated embodiment, the first drive shaft 60 passes through, but is not rotationally coupled to, the transmission gear 19, the final bevel gear 64, and the hollow drive shaft 62, so that the first drive shaft 60 directly drives the first flywheel 3*a*. Similar as in the FIGS. 1*a*, 1*b* and 4, the first vibration generating element is rotationally coupled to a motor 2. The second vibration generating element is rotationally coupled to a driving shaft of the rotation driving means, which is the motor 2, wherein in difference to the vibration generator of FIG. 5 the motor 2 spins the first and second imbalanced flywheels 3*a* and 3*b*. Again, the vibration transmission element 4 supports the first and second vibration generating elements.

Further, the vibration generator comprises means for adjusting a phase of the rotational movement of the two vibration generating elements. The means for adjusting a phase comprises a gear train transferring a rotation of the drive shaft to the second vibration generating element and thus the second imbalanced flywheel 3*b*, wherein the gear train comprises a phase-adjustment gear portion 18. The phase-adjustment gear portion 18 in particular comprises a bevel gear arrangement, wherein one beveled gear wheel of the beveled gear arrangement is displaceable around a longitudinal axis of the gear train to adjust a phase of rotation of the corresponding vibration generating element respectively imbalanced flywheel 3*b*.

In FIGS. 6, 7 and 8 a user-rotated amplitude adjustment ring 17 is then positioned on the outside of the dental handpiece, wherein, as can in particular be seen in FIG. 8, the amplitude adjustment ring 17 is surrounded on the outside of the dental handpiece 1 by the outer case 9. On the inside of the amplitude adjustment ring 17, the phase-adjustment gear portion 18 is mounted, wherein a bearing is not directly shown. A transmission gear 19, wherein a bearing is again not shown, transmits then the motion of the phase-adjustment gear portion 18 to a direction-reversal gear 20, which transmits the motion to a further bevel gear attached to the second imbalanced flywheel 3*b*.

On the other side, the first imbalanced flywheel 3*a* is directly driven by the motor 2.

To adjust the relative phase of the two imbalanced flywheels 3*a* and 3*b*, the amplitude adjustment ring 17 is rotated through which the phase-adjustment gear portion 18 and thus in particular the one beveled gear wheel of the bevel gear arrangement of the phase-adjustment gear 18 is moved to a different location around the perimeter of the transmission gear 19, as it is shown in the FIGS. 6 and 7. From both Figures, it is derivable that the position of the hole 5 of the second imbalanced flywheel 3*b* is moved through rotating the amplitude adjustment ring 17.

Regarding the relative phase of the two imbalanced flywheels 3*a* and 3*b* and the impact on the imbalance of both imbalanced flywheels 3*a* and 3*b*, it is referred to the explanations to the bottom part of FIG. 5, where it is explained in detail which impact different relative phases have.

It should be noted that the amplitude adjustments described above in view of the FIGS. 5-8 could be also applied to a dental handpiece 1 which is a dental scaler as shown in FIG. 1*b*. In addition, a further combination with the speed-increasing gear 15 shown in FIG. 4 would then be also possible.

Some embodiments also provide a method for manufacturing a corresponding dental handpiece, wherein the method comprises the steps of providing a rotation driving means, imbalancing an object, for example, drilling or milling a hole or pocket in it or grinding off part of it, to form an imbalanced vibrating portion, providing a vibration generating element rotationally coupled to the rotation driving means and comprising the imbalanced vibrating portion and providing a vibration transmission element in mechanical communication with the vibration generating element. The rotation of the vibration generating element causes the imbalanced vibrating portion to generate vibrations of the vibration transmission element, wherein the vibration transmission element is configured to deliver the vibrations to an object.

Figure 9:
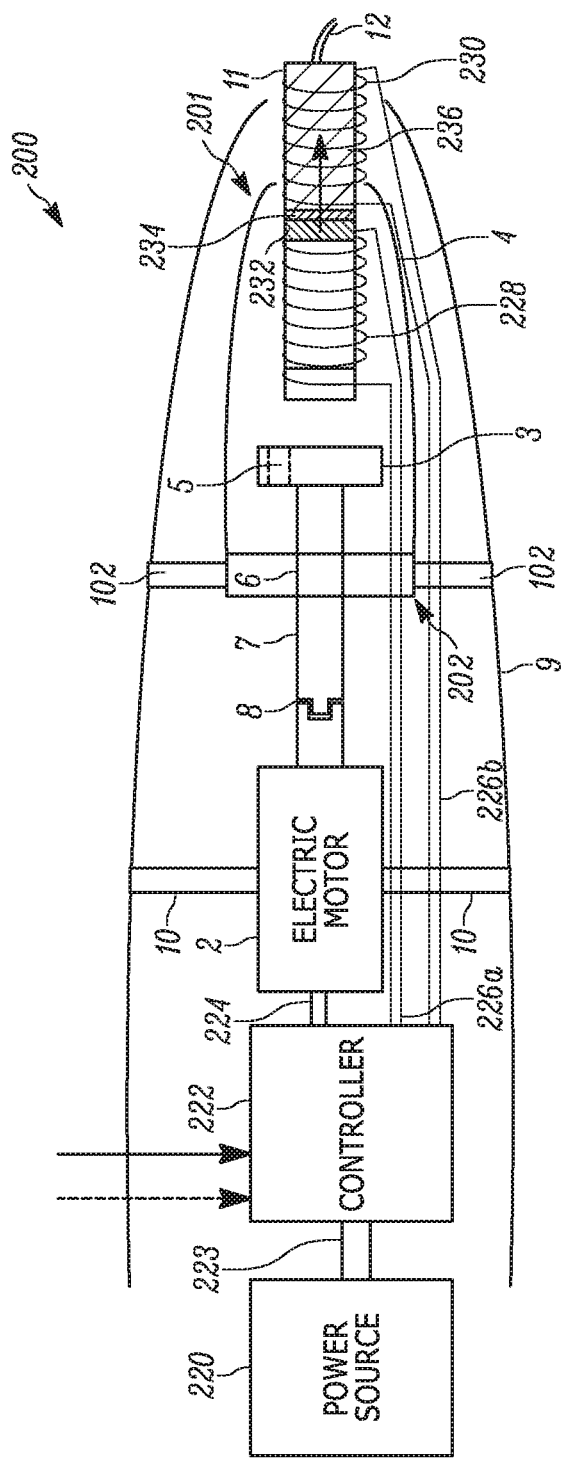
FIG. 9 shows a dental handpiece comprising a vibration generator and an electric dispenser for dispensing a material.

FIG. 9 shows a dental handpiece 200 for dispensing a pasty filler mass according to one embodiment. The dental handpiece 200 includes an electric dispenser 201 and a vibration generator 202. In the example of FIG. 9, the dental handpiece 200 includes some components that are the same as or similar to components of the dental handpiece 1 as described with respect to and illustrated in FIGS. 1*a* and 1*b*. In the example illustrated, dental handpiece 200 includes electric motor 2, imbalanced flywheel 3, vibration transmission element 4, imbalancing hole 5, bearing 6, driving shaft 7, rotational coupler 8, outer case 9, motor mounts 10, container 11, and tip 12 as described above, and as a consequence those above-described portions are not described again in greater detail below. In the example of FIG. 9, dental handpiece 200 further includes a power source 220 that is connected to a controller 222 via electrical links 223 (for example, wires 223). The controller 222 may be, for example, a microcontroller (with memory and input/output components on a single chip or within a single housing) or may include separately configured components, for example, a microprocessor, memory, and input/output components. The controller 222 may also be implemented using other components or combinations of components including, for example, a digital signal processor (DSP), an application specific integrated circuit (ASIC), a field-programmable gate array (FPGA), or other circuitry. The controller 222 is connected to the electric motor 2 via electrical links 224 (for example, wires 224). As will be described in greater detail, the controller 222 generates control signals that are transmitted via electrical links 226A and 226B (for example, wires 226A and 226B and collectively "wires 226") to coil 228 and coil 230. The coils 228 and 230 surround a magnet 232. As is explained in greater detail below, a piston 234 is driven as a result of an electromagnetic actuation, and a material 236 is dispensed from the container 11 of the dental handpiece 200. In the embodiment illustrated, the controller 222, electrical links 223, electrical links 226, coil 228, coil 230, magnet 232, and piston 234 form an electric dispenser 201.

Power source 220 provides electrical power to controller 222 and may be implemented using one or more known devices, for example, one or more non-rechargeable batteries, rechargeable batteries, power supplies (input power not shown but familiar to those skilled in the art), or other devices that are capable of providing electrical power to controller 222.

Electrical links 223, 224, and 226 may be implemented, for example, using wires, electrical traces, or other physical components. Wires 226 form coils 228 and 230 around container 11. Although wires 226 are illustrated separately as wires 226A and 226B, in some examples, wires 226A and wires 226 may be in series and wound around in opposite directions to form coils 228 and 230. In this way, in these examples, when the controller 222 provides a current through wires 226, coils 228 and 230 may generate magnetic fields with opposite polarities. In other examples, if wires 226A and 226B are not in series and not wound in opposite directions, then controller 222 may provide current in opposite directions through wires 226A and 226B, and coils 228 and 230 may also generate magnetic fields with opposite polarities. In yet other examples, if wires 226A and 226B are not in series and wound in opposite directions, then controller 222 may provide current in the same direction through wires 226A and 226B, and coils 228 and 230 may also generate magnetic fields with opposite polarities.

The memory of controller 222 may include computer-readable instructions that, when executed by the electronic processor of controller 222, cause controller 222 and, more particularly the electronic processor, to perform or control the performance of various functions or methods attributed to controller 222 herein (for example, dispensing of material from the tip 12, vibrating container 11 that contains the material). The memory may include transitory, non-transitory, volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital or analog media. The functions attributed to controller 222 herein may be embodied as software, firmware, hardware or a combination thereof.

Controller 222 is electrically connected to electric motor 2 via electrical links 224. The controller 222 may control electric motor 2, via electrical links 224, to operate rotational coupler 8 at different speeds. Rotational coupler rotates imbalanced flywheel 3 to cause vibration transmission element 4 to vibrate and deliver the vibrations to container 11 and material 236. Upon receiving the vibrations from vibration transmission element 4, a property of material 236 changes. For example, the viscosity of material 236 may change due to the vibrations received from vibration transmission element 4 and imbalanced flywheel 3.

Controller 222 may also control the position of magnet 232 with current supplied to coils 228 and 230 from the power source 220. For example, current controlled by the controller 222 may create a magnetic field gradient. In some examples, electric dispenser 201 (formed by magnet 232 and coils 228 and 230 and controlled by the controller 222) operates as a linear electromagnetic actuator, such as a moving magnet actuator (MMA). In these examples, magnet 232 may be an axially-oriented cylindrical permanent magnet positioned between two iron pole pieces to form the mover or actuator of the MMA. Additionally, in some examples, coils 228 and 230 may be two oppositely wound coils connected in series and in mechanical communication with a back iron (not shown) to form the stator of the MMA.

For example, controller 222 may provide a current through each of coils 228 and 230 to generate a magnetic field gradient created as a result of the magnetic field generated at each of coils 228 and 230. In some examples, the amount of current provided through each of coils 228 and 230 is pre-determined and programmed into or otherwise established in controller 222. As illustrated in FIG. 9, coil 228 generates a magnetic field that magnetically repels magnet 232 away from coil 228 and coil 230 generates a magnetic field that magnetically attracts magnet 232 towards coils 230, causing magnet 232 to receive a force as indicated by the arrow. In other words, coils 228 and 230 each generate a magnetic field that are opposite in polarity from each other to form a magnetic field gradient that applies a Lorentz force on magnet 232 proportional to the coil current.

The magnetic force that causes magnet 232 to move also causes piston 234 and material 236, which are mechanically linked to magnet 232, to move. In this way, controller 222 can dispense material 236 from tip 12 by moving magnet 232 closer to tip 12. In some examples, dispensing material 236 from tip 12 may not be possible or practical until a property of material 236 has changed due to the vibrations received by material 236 from vibration transmission element 4. For example, electric dispenser 201 may not be able to dispense material 236 from tip 12 until a viscosity of material 236 has been lowered due to the vibrations received by material 236 from vibration transmission element 4.

Figure 10A:
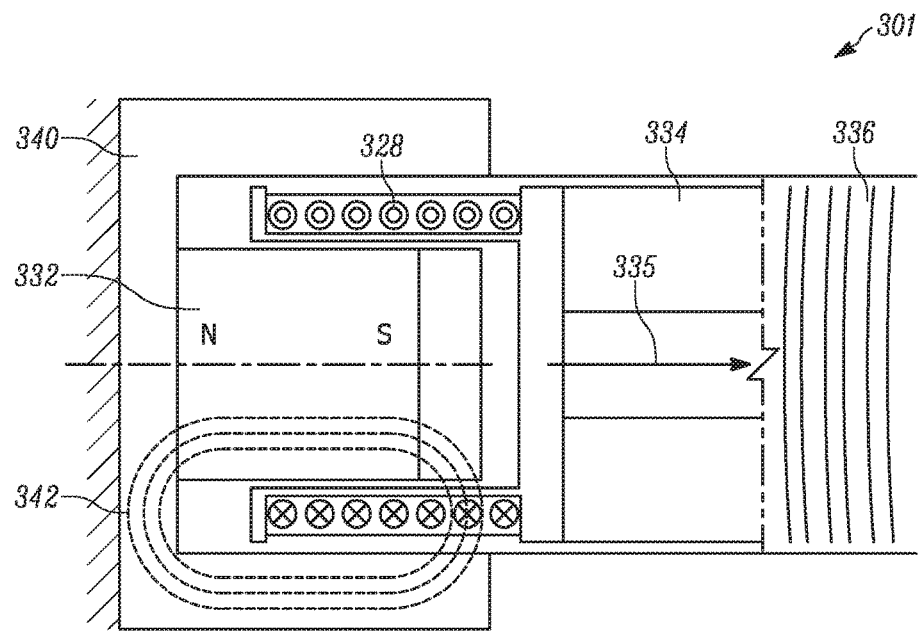
FIG. 10a shows another example of the electric dispenser.

FIG. 10a shows another embodiment of an electric dispenser, namely electric dispenser 301. The electric dispenser 301 includes coil 328, magnet 332, piston 334 mechanically connected or linked to the coil 328, and material 336. The electric dispenser 301 also includes a back iron 340 mechanically connected or linked to the magnet 332. Many components of the electric dispenser 301 are similar to the components of electric dispenser 201. However, electric dispenser 301 operates as a different type of linear electromagnetic actuator, namely a voice coil actuator (VCA), and not as a MMA. Magnetic flux lines 342 illustrate a magnetic field that may be generated in a portion of coil 328.

The controller 222 may control the position of the piston 334, by creating a magnetic field with the coil 328 using electrical power from the power source 220. For example, the controller 222 may provide a current through the coil 328 to generate a magnetic field as illustrated by the magnetic flux lines 342. In some examples, the controller 222 may provide a pre-determined amount of current through the coil 328.

As illustrated in FIG. 10a, the interaction of the magnetic field of the magnet 332 and the magnetic field generated by the coil 328 may cause the piston 334 (the mover or actuator of the VCA) to move away from the magnet 332 and the back iron 340 (the stator of the VCA) in the direction indicated by the arrow 335. In some examples, the magnet 332 may be positioned between the back iron 340 and a pole piece.

The material 336 is mechanical contact or communication with the piston 334. As a consequence, the force applied to the coil 328 and the piston 334 is also applied to the material 336. The electric dispenser 301 can dispense the material 336 from tip 12 by moving the piston 334 closer to the tip 12.

Figure 10B:
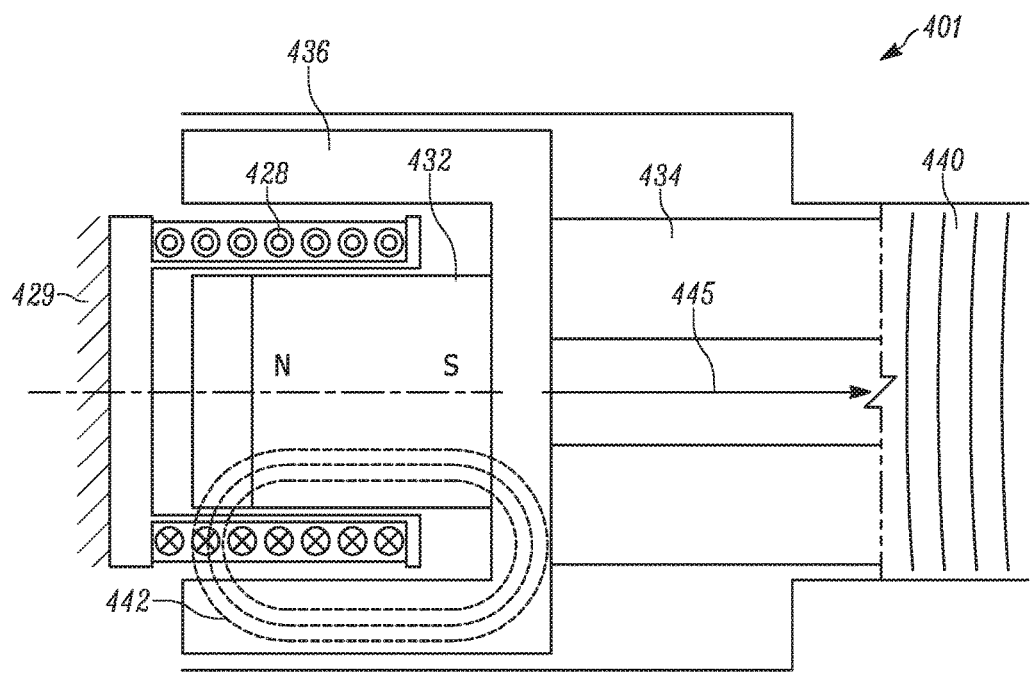
FIG. 10b shows yet another example of the electric dispenser.

FIG. 10b shows yet another example of an electric dispenser, namely electric dispenser 401. The electric dispenser 401 includes coil 428. The coil 428 is held in position at least in part by a wall 429. The electric dispenser 401 includes magnet 432 and a back iron 436 that is mechanically connected or linked to the magnet 432. A piston 434 is mechanically connected or linked to the back iron 436. Piston 434 is in contact with or in mechanical communication with material 440. A number of components of electric dispenser 201 are similar to components in electric dispenser 201. However, the electric dispenser 401 does not operate as an MMA. Instead, the electric dispenser 401 operates as a different type of linear electromagnetic actuator, namely an inverted voice coil actuator (IVCA). Magnetic flux lines 442 illustrate a magnetic field that may be generated in a portion of coil 428.

The controller 222 controls the position of the piston 434 (which is attached to the back iron 436 and the magnet 432), by creating a magnetic field with the coil 428 using electrical power from the power source 220. For example, the controller 222 may provide a current through the coil 428 to generate a magnetic field as illustrated by magnetic flux lines 442. In some examples, the controller 222 may provide a pre-determined amount of current through the coil 428.

As illustrated in FIG. 10b, the magnetic field generated by the coil 428 repels the magnetic field generated by the magnet 432, causing the magnet 432, back iron 440, and the piston 434 (for example, the actuator or mover of the IVCA) to move away from the coil 428 and wall 429 (the stator of the IVCA). The magnet 432, back iron 440, and piston 434 move in a direction indicated by the arrow 445. Compared to the electric dispenser 301, the electric dispenser 401 is considered an inverted VCA because the coil 428 is a stator rather than an actuator, and the magnet 432 and back iron 440 are a mover rather than a stator.

The force applied to the magnet 432, the back iron 440, and the piston 434 is also applied to the material 436, which is in mechanical communication with the piston 434. In this way, the electric dispenser 401 can dispense the material 436 from a tip 12 by moving the piston 434 closer to the tip 12.

Figure 11:
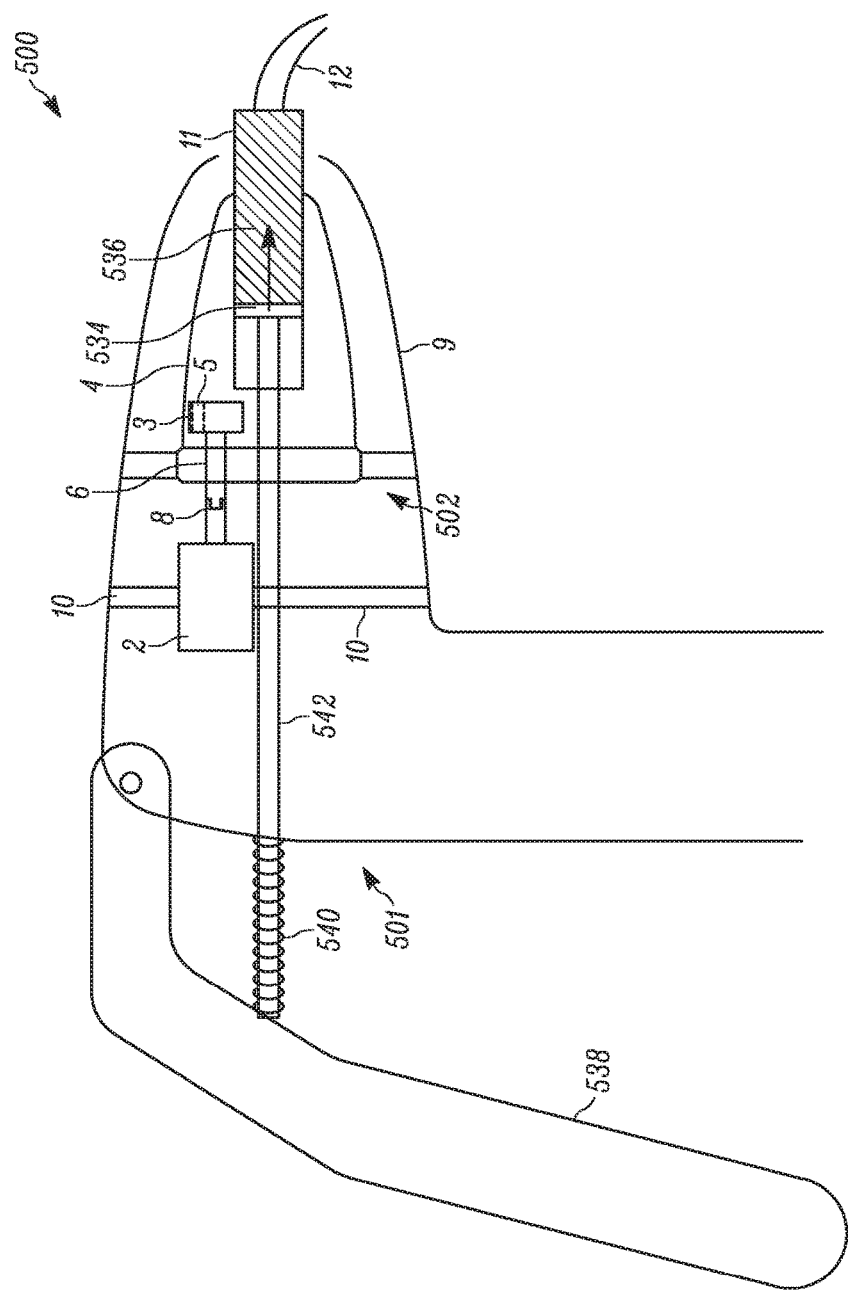
FIG. 11 shows a dental handpiece comprising a vibration generator and a manual dispenser for dispensing a material.

FIG. 11 shows a dental handpiece 500 for dispensing a pasty filler mass according to another embodiment. The dental handpiece 500 includes a manual dispenser 501 and a vibration generator 502. As illustrated in the example of FIG. 11, the dental handpiece 500 includes some components that are same as or similar to components of the dental handpiece 1 as described and illustrated FIGS. 1a and 1b, including the electric motor 2, the imbalanced flywheel 3, the vibration transmission element 4, the imbalancing hole 5, the bearing 6, the driving shaft 7, the rotational coupler 8, the outer case 9, the motor mounts 10, the container 11, and the tip 12. In the example of FIG. 11, the dental handpiece 500 also includes piston 534 and material 536. In contrast to electric dispenser 201 of FIG. 9, in the example of FIG. 11, the dental handpiece 500 includes a squeeze handle 538, a spring 540, and a pushrod 542 that in combination with the piston 534 form the manual dispenser 501.

In one example, the electric motor 2 is configured to operate the rotational coupler 8 at different speeds. The rotational coupler 8 rotates the imbalanced flywheel 3 to cause the vibration transmission element 4 to vibrate and deliver the vibrations to the container 11 and the material 536. Upon receiving the vibrations from the vibration transmission element 4, a property of the material 536 changes. For example, the viscosity of the material 536 may be lowered due to the vibrations received from the vibration transmission element 4 and the imbalanced flywheel 3.

The squeeze handle 538 controls the position of the piston 534 with the pushrod 542. The squeeze handle 538 applies a force to the pushrod 542. In some examples, the spring 540 provides a force to maintain the squeeze handle 538 open or on in a biased position when no force is applied to the squeeze handle 538. When a force is applied to the squeeze handle 538, for example, by manually squeezing it, a force is applied to the pushrod 542. This force is also applied to the piston 534. The piston 534 is in contact with or mechanical communication with the material 536. Material 536 is dispensed from the tip 12 when the pushrod 542 is moved closer to the tip 12 as a result of the force provided by the squeeze handle 538. In some examples, the force that may be applied via the squeeze handle 538 may not be of a sufficient magnitude to dispense the material 536 from the tip 12 until a property of the material 536 has changed due to the vibrations received from the vibration transmission element 4. For example, dispensing the material 536 from the tip 12 using the squeeze handle 538 may be impossible or difficult until a viscosity of the material 536 has been lowered due to the vibrations received by the material 536 from the vibration transmission element 4 and the imbalanced flywheel 3.

Figure 12:
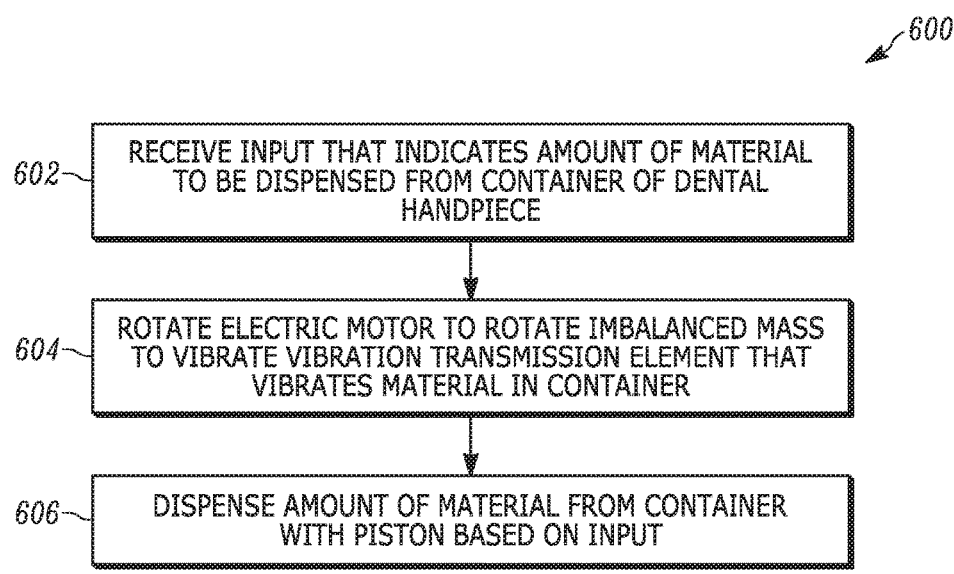
FIG. 12 shows a flow chart of a method for dispensing a material from a container within a dental handpiece.

FIG. 12 illustrates a flow chart of a method 600 for dispensing a material from a container 11 within a dental handpiece 200 according to one embodiment. The method 600 of FIG. 12 is described with reference to the electric dispensers 201, 301, and 401 of FIGS. 9-10b, respectively. However, portions of the method 600 of FIG. 12 may also be applicable to manual dispenser 501 of FIG. 11. In particular, the rotation of the imbalanced flywheel 3 to cause the vibration transmission element 4 to vibrate and, in turn, to cause the material 236 to vibrate is applicable to manual dispenser 501 of FIG. 11.

The method 600 includes the controller 222 receiving an input to dispense material 236 from the container 11 (block 602). In response to the input, the controller 222 causes or controls the electric motor 2 to rotate the imbalanced flywheel 3. The rotation of the imbalanced flywheel 3 vibrates the vibration transmission element 4, which, in turn, vibrates the material 236 in the container 11 (block 604). The controller 222 then dispenses a predetermined amount of the material 236 from the container 11 with the piston 234 (block 606).

In other embodiments, two separate inputs are used to control the electric dispenser 201, 301, or 401. In such embodiments, a first input is received by the controller 222. In response to receiving the first input, the controller 222 controls the electric motor 2 to rotate the imbalanced flywheel 3. As noted, rotation of the imbalanced flywheel 3 vibrates the vibration transmission element 4, which, in turn, vibrates the material 236 in the container 11. The controller 222 then receives a second input that indicates the amount of the material 236 to be dispensed from the container 11. The controller 222 then causes the amount of the material 236 to be dispensed from the container 11 based on the second input. In some examples, the single input or the two inputs can be a signal or signals from a push button or other suitable actuation device that can provide the controller 222 with input.

In some examples, the controller 222 controls at least the coils 228 and 230 to generate a magnetic field gradient that applies a force on the magnet 232, which, in turn, causes the piston 234 to move. In some examples, the controller 222 controls the coil 328 of FIG. 10a to generate a magnetic field that applies a force on the coil 328 that moves the piston 334 of FIG. 10a away from the magnet 332. In other examples, the controller 222 controls the coil 428 of FIG. 10b to generate a magnetic field that applies a force on the magnet 432 that causes the piston 434 to move away from the coil 428.

Figure 13:
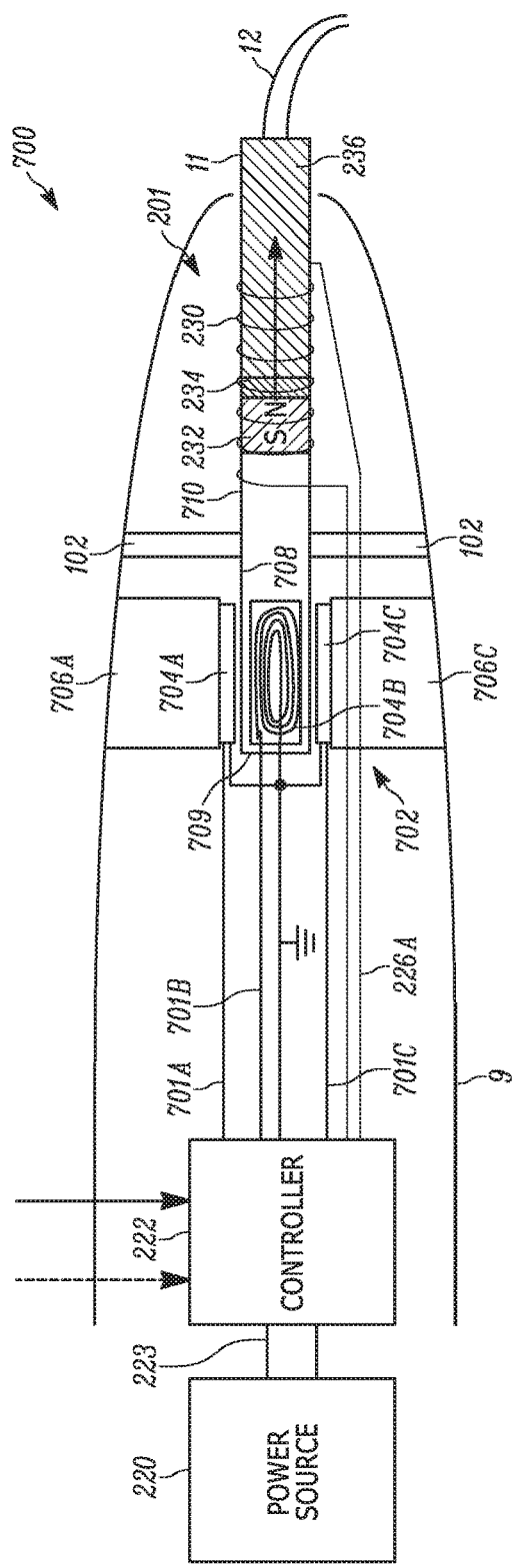
FIG. 13 shows another example of a dental handpiece for dispensing a pasty filler mass comprising a vibration generator.

FIG. 13 shows another example of a vibration generator 702 of a dental handpiece 700. The dental handpiece 700 has some components that are similar to the components of the dental handpiece 200 as described above. As consequence, the similar components between the dental handpieces 200 and 700 are not described again in greater detail. The controller 222 provides a stator current via electrical links 701A, 701B, and 701C (for example, wires 701A, 701B, and 701C and collectively "wires 701"). The wires 701A, 701B, and 701C form a first stator coil 702A, a second stator coil 702B, and a third stator coil 702C, respectively. In the example of FIG. 13, instead of an electric motor (for example, the electric motor 2 as described above), the dental handpiece 700 includes the first stator coil 704A, the second stator coil 704B, and the third stator coil 704C (collectively described as a "set of stator coils 704") arranged on corresponding stator coil mounts 706A, 706B, and 706C (collectively described as "stator coil mounts 706"). Each of the stator coils 704 is energized (i.e., driven) by the controller 222 when the controller 222 provides a respective stator current through each of the stator coils 704. The controller 222 is powered by a power source 220 (for example, a battery).

In one embodiment, the vibration generator 702 includes a conductive member 708 (for example, a cylinder) disposed between the set of stator coils 704. The set of stator coils 704 is energized (i.e., driven) by the controller 222 in a sequence to generate a rotating magnetic field 710.

Figure 14A:
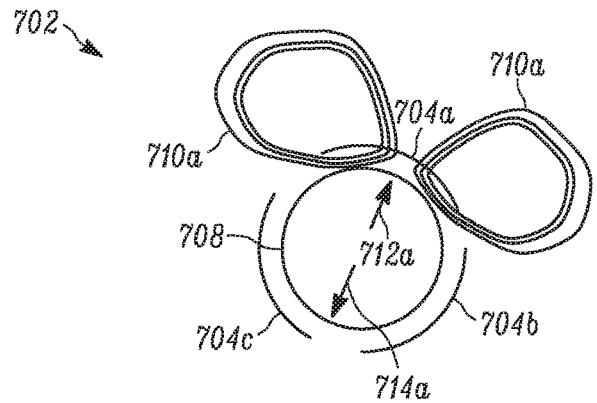
FIGS. 14a-14c show the operation of the vibration generator of FIG. 13.

As may be understood by reference to FIG. 14*a*, the controller 222 energizes the first stator 704A at a first time (for example, time T1). This results in the generation of a magnetic field 710A. The magnetic field 710A induces eddy currents 712A in the conductive member 708 disposed near the first stator coil 704A. The induced eddy currents 712A oppose the generated magnetic field 710A and cause a repulsive force 714A that acts upon the conductive member 708.

Figure 14B:
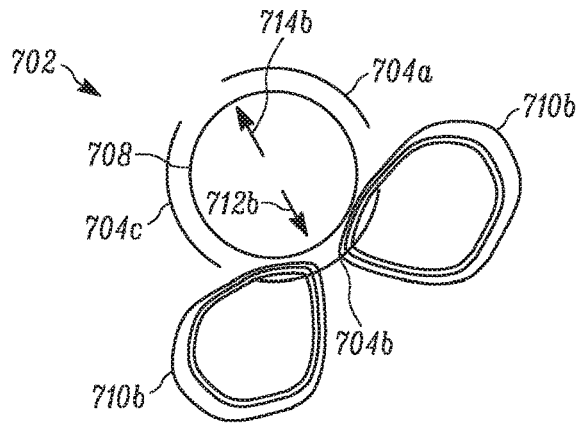

As may be understood by reference to FIG. 14*b*, the controller 222 energizes the second stator coil 704B at a second time (for example, a time T2) to generate a magnetic field 710B. The magnetic field 710B induces eddy currents 712B in the conductive member 708 disposed near the second stator coil 704B. The induced eddy currents 712B oppose the generated magnetic field 710B and cause a repulsive force 714B that acts upon the conductive member 708.

Figure 14C:
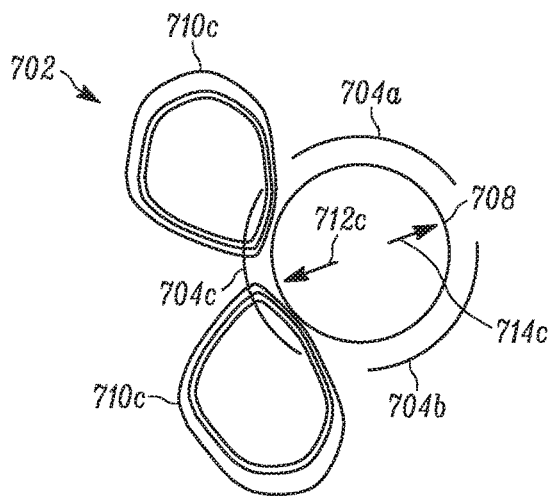

With reference to FIG. 14*c*, the controller 222 energizes the third stator coil 704C at a third time (for example, a time T3) to generate a magnetic field 710C. The magnetic field 710C induces eddy currents 712C in the conductive member 708 disposed near the third stator coil 704C. The induced eddy currents 712C oppose the generated magnetic field 710C and cause a repulsive force 714C that acts upon the conductive member 708. When the first, second, and third stator coils are energized quickly in succession, a rapidly changing (for example, a frequency of several kilohertz (kHz) or higher) rotating magnetic field may be generated in the form of rotating magnetic field 710. The rotating magnetic field 710 induces eddy currents 712A-712C in the conductive member 708 as described above. The induced eddy currents 712A-712C expel the respective rotating magnetic fields 710A-710C to create repulsive forces 714A-714C between the conductive member 708 and each of the stator coils 704 in sequence. The repulsive force (for example, one of the repulsive forces 714A-714C) rotates with the rotating magnetic field and vibrates the conductive member 708. It is understood that although the controller 222 is described as generating a rotating magnetic field in the vibration generator 702 to generate vibrations (i.e., to generate repulsive forces) of the conductive member 708, the controller 222 may also generate a non-rotating magnetic field in the vibration generator 702 to generate vibrations of the conductive member 708. For example, the controller 222 may energize the set of stator coils 704 in other sequences that generate a non-rotating magnetic field that generates vibrations in the conductive member 708.

With reference to FIG. 13, the conductive member 708 has a first end 709 and a second end 710. The first end 709 is adjacent to and disposed within the set of stator coils 704. The second end 710 of the conductive member 708 is configured to hold the capsule 11 containing the magnet 232, the piston 234, and the material 236. The vibrations generated by the vibration generator 702 are transmitted from the first end 709 of the conductive member 708 to the capsule 11 disposed at the second end 710 of the conductive member 708. The transmitted vibrations vibrate the capsule 11 and activate the thixotropic properties of the material 236. For example, in some embodiments, the transmitted vibrations reduce the viscosity of the material 236, which allows the material 236 to be dispensed from the tip 12.

In some embodiments, the conductive member 708 may be formed from a material with high conductivity. For example, the conductive member 708 may be formed from copper, aluminum, or other suitable conductive material. In the example of FIG. 13, no magnetic material is used in the vibration generator 702, resulting in greater simplicity and robustness, and lower cost.

Figure 15:
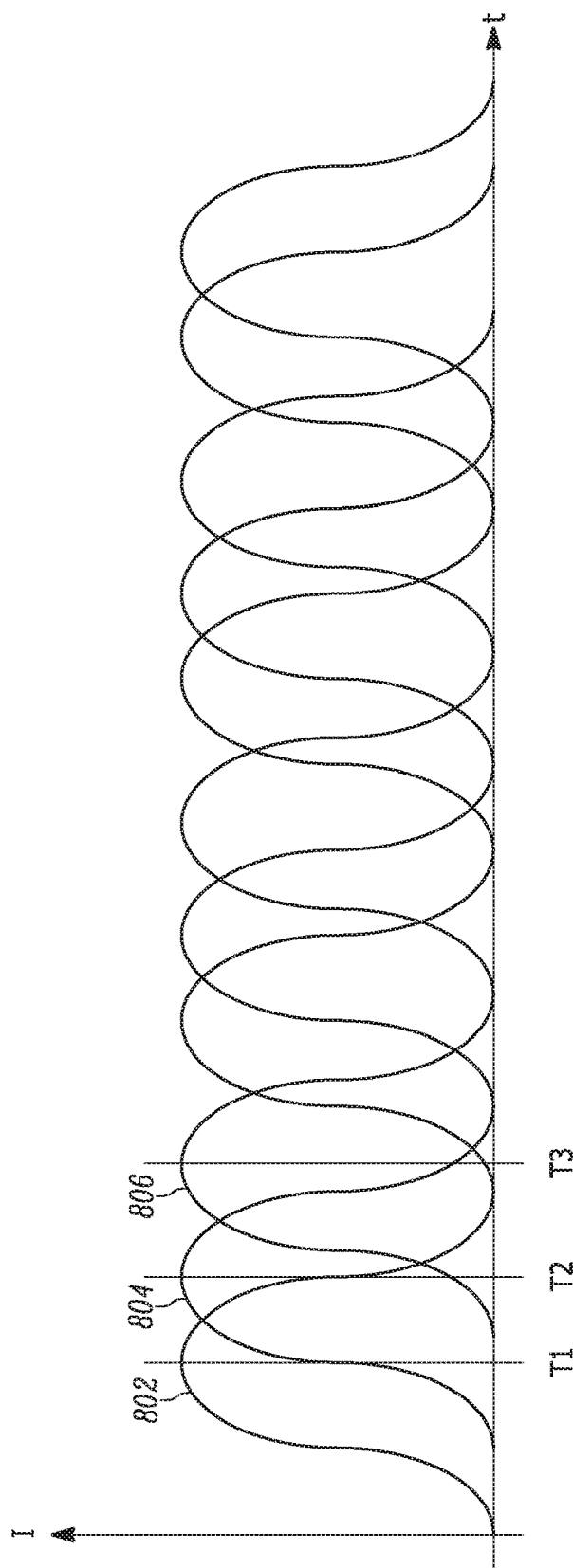
FIG. 15 shows a timing diagram of respective stator currents driven through the stator coils of FIG. 13 as a function of time.

FIG. 15 shows a timing diagram of respective stator currents driven through the stator coils 704 of FIG. 13 as a function of time. In the example of FIG. 15, the timing chart 800 includes a first stator current 802, a second stator current 804, and a third stator current 806. In some embodiments, the first stator current 802 is driven through the stator coil 704A, the second stator current 804 is driven through the stator coil 704B, and the third stator current 806 is driven through the stator coil 704C. As illustrated in FIG. 15, a maximum amount of the first stator current 802 passes through the first stator coil 704A at a time T1 before a time T2 and a time T3. Additionally, a maximum amount of the second stator current 804 passes through the second stator coil 704B at the time T2, which is after the time T1 and before the time T3. Likewise, a maximum amount of the third stator current 806 passes through the third stator coil 704C at time T3, which is after the times T1 and T2. In one particular example, the respective stator currents 802-806 are one hundred and twenty degrees out of phase with each other. In this way, the stator currents 802-806 allow the stator coils 704 to generate a rotating magnetic field in which variations of the field are periodic.

Figure 16:
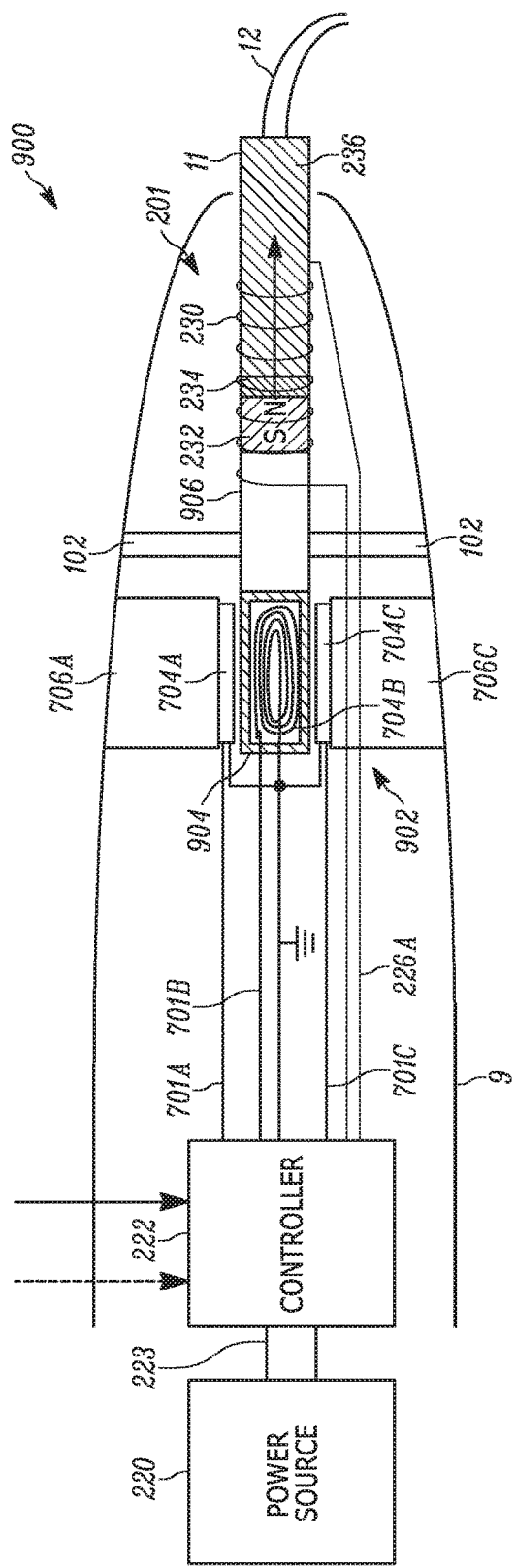
FIG. 16 shows yet another example of a vibration generator of a dental handpiece.

FIG. 16 shows yet another example of a vibration generator 902 of a dental handpiece 900. Components of the dental handpiece 900 that are similar to the components of the dental handpieces 900 and 200 are not described in detail. In the example of FIG. 16, instead of a conductive member (for example, the conductive member 708 as described above), the dental handpiece 900 includes a magnetic member 904. The magnetic member 904 (for example, a cylinder) is disposed between the set of stator coils 704. The set of stator coils 704 is energized (i.e., driven) by the controller 222 in a sequence to generate a rotating magnetic field 910 as described in greater detail below and illustrated in FIGS. 17*a*-17*c*.

Figure 17A:
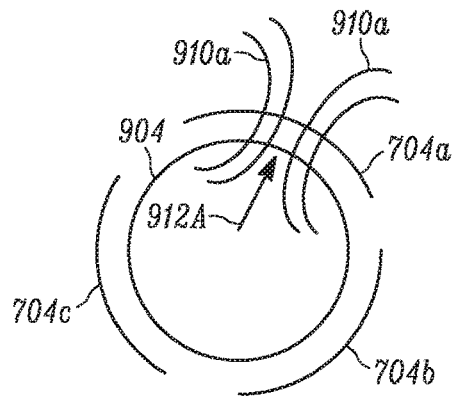
FIGS. 17a-17c show the operation of the vibration generator of FIG. 16.

As may be understood by reference to FIG. 17*a*, the controller 222 energizes the first stator coil 704A to generate a magnetic field 910A. The magnetic field 910A magnetically attracts the magnetic member 904 disposed near the first stator coil 704A and is represented as an attraction force 912A that acts on the magnetic member 904.

Figure 17B:
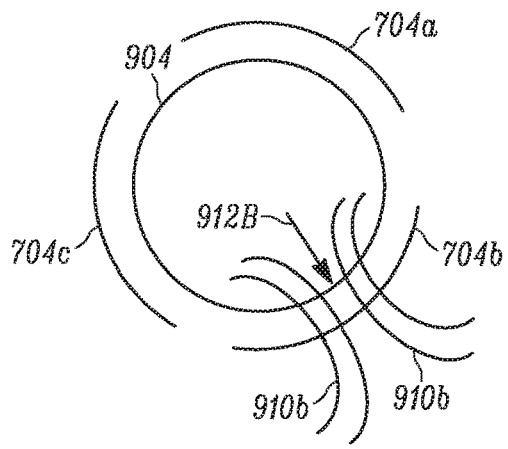

As illustrated in FIG. 17b, after energizing the first stator coil 704A, the controller 222 energizes the second stator coil 704B to generate a magnetic field 910B. The magnetic field 910B magnetically attracts the magnetic member 904 disposed near the second stator coil 704B and is represented as an attraction force 912B that acts on the magnetic member 904.

Figure 17C:
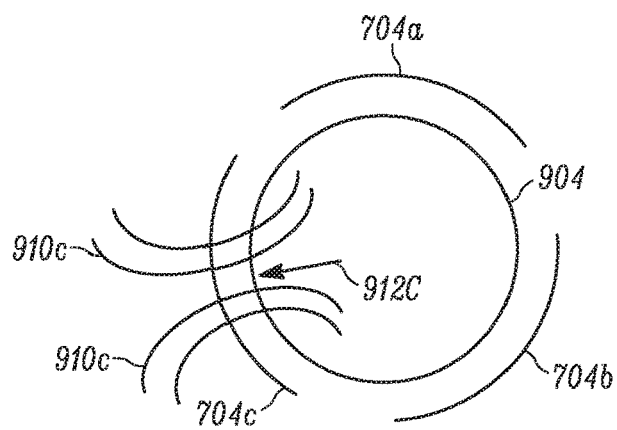

As illustrated in FIG. 17c, after energizing the first and second stator coils 704A and 704B, the controller 222 energizes the third stator coil 704C to generate a magnetic field 910C. The magnetic field 910C magnetically attracts the magnetic member 904 disposed near the third stator coil 704C and is represented as an attraction force 912C that acts on the magnetic member 904. The controller 222 may energize the first, second, and third stator coils 704A, 704B, and 704C in quickly in succession to create rapidly changing (for example, a frequency of several kilohertz (kHz)) or higher) rotating magnetic field. The rotating magnetic field 910 magnetically attracts the magnetic member 904 as described above. The attraction is represented by attraction forces 914A-914C between the magnetic member 904 and each of the stator coils 704 in sequence. The magnetic attraction force (for example, one of the attraction forces 914A-914C) rotates with the rotating magnetic field 910 and vibrates the magnetic member 904 and a second member 906. Instead of creating a rotating magnetic field, the controller 222 may energize the set of stator coils 704 in other sequences that generate a non-rotating magnetic field that generates vibrations in the magnetic member 904.

As illustrated in FIG. 16, the magnetic member 904 is connected to the second member 906 that is supported by mounts 102. The magnetic member 904 is adjacent to and disposed within the set of stator coils 704. The second member 906 in addition to supporting the magnetic member 904 within the set of stator coils 704 is also configured to hold the capsule 11 containing the magnet 232, the piston 234, and the material 236. The vibrations generated by the vibration generator 902 are transmitted from the magnetic member 904 to the capsule 11 held by the second member 906. The transmitted vibrations vibrate the capsule 11 and activate the thixotropic properties of the material 236. For example, in some embodiments, the transmitted vibrations reduce the viscosity of the material 236, which allows the material 236 to be dispensed from the tip 12.

In some embodiments, the magnetic member 904 may be formed from a magnetic material. For example, the magnetic material can include ferrite, iron, steel, ferritic stainless steel, or other suitable magnetic material. In other embodiments, the magnetic member 904 is a permanent magnet. In these embodiments, it is understood that the permanent magnet would be either attracted or repelled by the rotating magnetic field 910, depending on the relative polarities of the magnetic member 904 and the electrically driven set of stator coils 704. Accordingly, a rotating attractive or repulsive force is generated by the vibration generator 902 to vibrate the magnetic member 904 and the second member 906.

Figure 18:
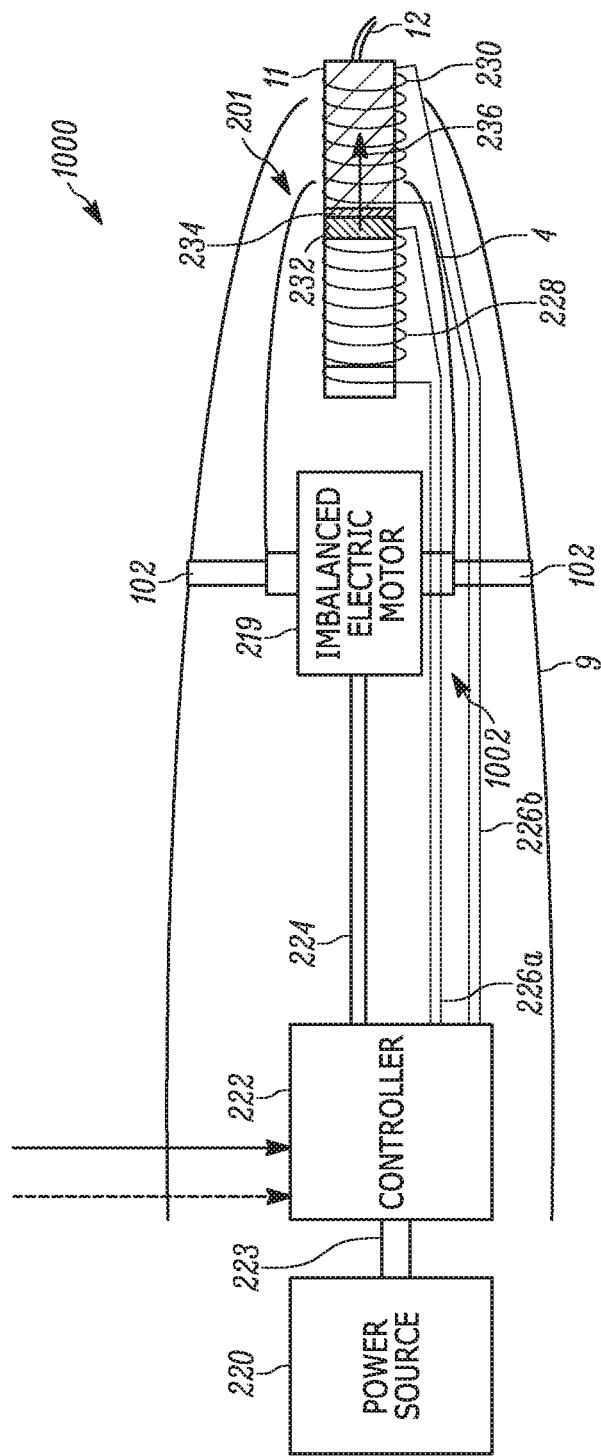
FIG. 18 shows another example of a vibration generator of a dental handpiece.

FIG. 18 shows another example of a vibration generator 1002 of a dental handpiece 1000. Components of the dental handpiece 1000 that are similar to the components of the dental handpiece 200 are not described in detail. The controller 222 is electrically connected to an imbalanced electric motor 219 via electrical links 224. The imbalance electric motor 219 may include a rotor that is imbalanced by removing mass from the rotor (for example, drilling an aperture or grinding material off of the magnetic core). In another example, the rotor of the imbalanced electric motor 219 is imbalanced by adding weight to the rotor. In yet another example, the rotor of the imbalanced electric motor 219 is imbalanced by forming the rotor in an imbalanced shape (for example, forming the magnetic core in an imbalanced shape). The imbalanced electric motor 219 can be used in place of or in combination with the imbalanced flywheel 3.

The controller 222 may control the imbalanced electric motor 219, via electrical links 224, to rotate at an adjustable speed. The motor 219 directly vibrates the vibration transmission element 4, which delivers the vibrations to container 11 and material 236. When the material 236 receives vibrations from vibration transmission element 4, a property of the material 236 (for example, the viscosity) changes.

Figure 19:
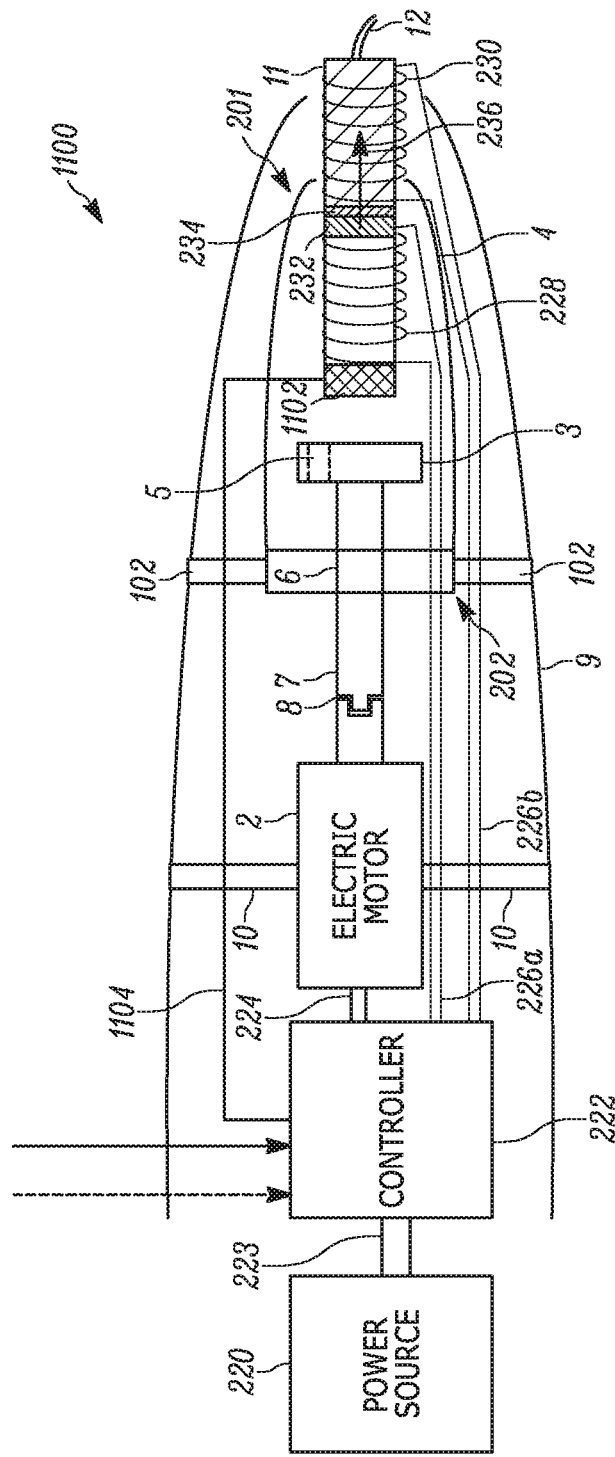
FIG. 19 shows another example of a dental handpiece.

FIG. 19 shows another example of a dental handpiece 1100. Components of the dental handpiece 1100 that are similar to the components of the dental handpiece 200 are not described again in detail. The dental handpiece 1100 includes a material identification component 1102 that is proximate to the container 11.

In some embodiments, the material identification component 1102 is a bar code reader that can read a bar code disposed on the surface of the container 11. The bar code includes an indication of the type of the material 236 in the container 11. In alternative embodiments, the material identification component 1102 includes a mechanical feature that when compressed by a corresponding mechanical feature on the container 11 is indicative of the type of the material 236. In other embodiments, the material identification component 1102 includes electrical contact pins that mate to a corresponding feature disposed on the container 11 that is indicative of the type of the material 236. In yet other embodiments, the material identification component 1102 includes a magnetic sensor that detects a magnetic feature of the container 11 that is indicative of the type of the material 236. In other embodiments, the material identification component 1102 includes a radio frequency identification (RFID) reader that detects an RFID tag disposed on the container 11 that is indicative of the type of the material 236.

The memory of controller 222 may include computer-readable instructions that, when executed by the electronic processor of controller 222, cause controller 222 and, more particularly the electronic processor, to perform or control the performance of various functions or methods attributed to controller 222 herein (for example, identifying the type of the material 236, determining whether the material 236 is suitable for pre-mixing). The functions attributed to controller 222 herein may be embodied as software, firmware, hardware or a combination thereof. In some embodiments, one or more look-up tables are stored in the memory of the controller 222. The one or more look-up tables contain information whether a particular type of the material 236 is suitable for pre-mixing.

Controller 222 is electrically connected to the material identification component 1102 via electrical link 1104 that is similar to the electrical links 224 as described above. The controller 222 may receive a signal, via electrical links 224, that is indicative of the type of the material 236. Upon receiving the signal from the material identification component 1102, the controller 222 may identify the type of the material 236. Upon identifying the type of the material 236, the controller 222 may also determine whether the type of the material 236 is suitable for pre-mixing.

For example, the controller 222 controls the material identification component 1102 as a bar code reader to scan a bar code disposed on the container 11. The controller 222 receives the signal, via the electrical link 1104, indicative of the type of the material 236 and identifies the type of the material 236. That is, the controller 222 may correlate the signal from the bar code disposed on the container 11 to a look up table in the memory of the controller 222 to identify the type of the material 236. Upon identifying the type of the material 236, the controller 222 may determine whether the type of the material 236 is suitable for pre-mixing. That is, the controller 222 may correlate the type of the material 236 to a look up table in the memory of the controller 222 to determine whether the identified type of the material 236 is suitable for pre-mixing. In some embodiments, the material 236 in the look up table stored in the memory of the controller 222 includes a composite material, an acid based cement, or other suitable pre-mixing material.

In some embodiments, when the controller 222 determines that the type of the material 236 is not suitable for pre-mixing, the controller 222 may disable the pre-mix feature. That is, the controller 222 prevents the material 236 from being pre-mixed. Conversely, when the controller 222 determines that the type of the material 236 is suitable for pre-mixing, the controller 222 may initiate the pre-mixing feature. That is, the controller 222 activates the vibration generator to pre-mix the material 236 in the container 11 prior to the controller 222 controlling the position of magnet 232 with current supplied to coils 228 and 230 from the power source 220 to dispense the material 236 as described above.

Alternatively, in some embodiments, when the controller 222 determines that the type of the material 236 is suitable for pre-mixing, the controller 222 may provide an indication to a user of the dental hand piece 1100 that the pre-mixing feature may be activated. In one example, the controller 222 activates an indicator (for example, a light or other suitable indicator that is disposed on the housing 9) that provides an indication to a user that the material 236 in the container 11 may be pre-mixed. After receiving the indication that the material 236 is suitable for pre-mixing, a user may control the controller 222 with a user input (the arrows into the controller 222) to activate the motor to vibrate the compound, thus mixing it, before controlling the position of magnet 232 with current supplied to coils 228 and 230 from the power source 220 to dispense the material 236 as described above.

Figure 20:
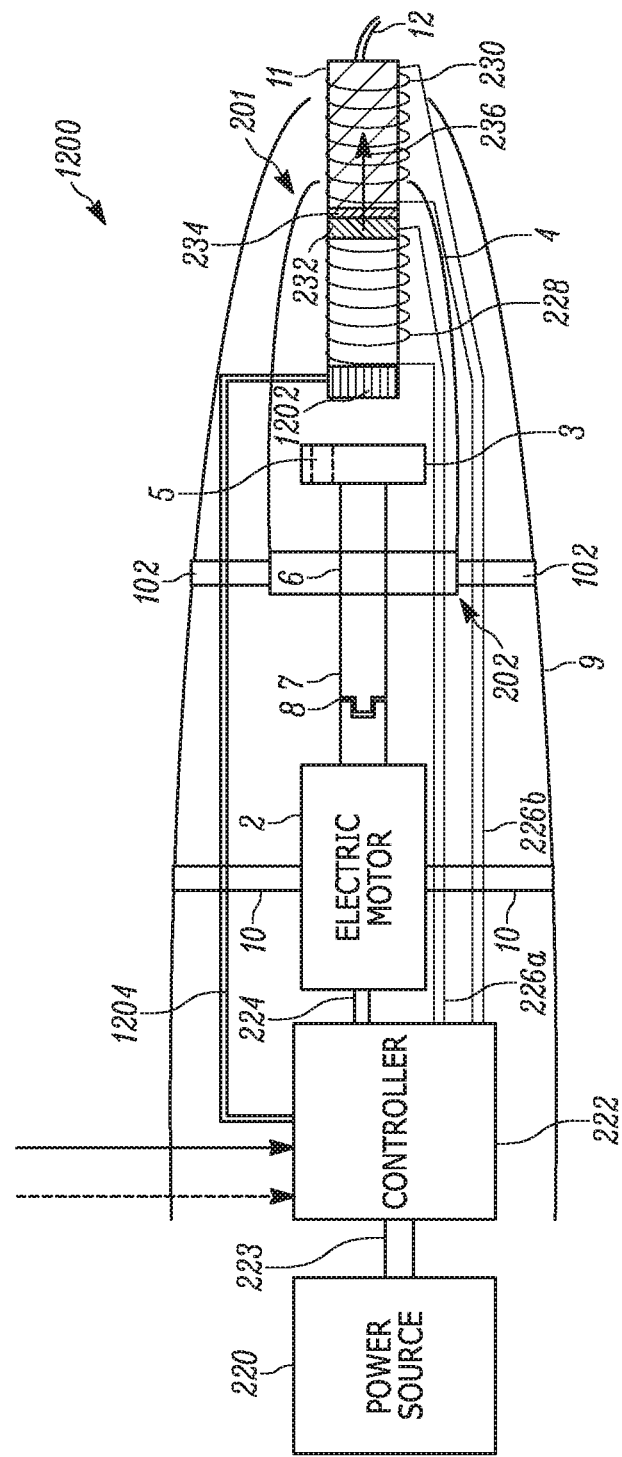
FIG. 20 shows another example of a dental handpiece.

FIG. 20 shows another example of a dental handpiece 1200. In addition to components that are similar to the components of the dental handpiece 200, dental handpiece 1200 further includes a heat source 1200 that is proximate to the container 11.

In some embodiments, the heat source 1200 is a resistive heat source. Controller 222 is electrically connected to the resistive heat source 1200 via electrical link 1204 that is similar to the electrical links 224 as described above. The controller 222 provides a current from the power source 220, via electrical links 224, causing a resistor in the resistive heat source 1200 to radiate heat toward the material 236 in the container 11. Alternatively, in some embodiments, the heat source 1200 is a chemical-based heat source. For example, the controller 222 controls a mixing component in the heat source 1200 that mixes chemicals together to cause a chemical reaction that produces a specific amount of heat.

In some embodiments, the controller 222 may provide an indication to a user of the dental hand piece 1100 that the heat source 1200 may be activated. For example, the controller 222 activates an indicator (for example, a light or other suitable indicator that is disposed on the housing 9) that provides an indication to a user that the heat source 1200 may radiate heat toward the material 236 in the container 11 (i.e., heat up the material 236 in the container 11).

In some embodiments, after receiving the indication that the heat source 1200 may be used to radiate heat, a user may control the controller 222 with a user input (the arrows into the controller 222) to control the amount of heat generated by and radiated from the heat source 1200. For example, the controller 222 receives a user input as described above and uses a look up table stored in the memory of the controller 222 to correlate the user input to a particular current that when provided to the heat source 1200 generates (i.e., radiates) a particular amount of heat from the heat source 1200. In a different example, the controller 222 receives a user input as described above and uses a look up table stored in the memory of the controller 222 to correlate the user input to a particular chemical mixture that when mixed together generates a particular amount of heat from the heat source 1200. The controller 222 may provide the particular current to the heat source 1200 or control the mixing component in the heat source 1200 to generate the amount of heat that correlates with the user input.

In alternative embodiments, the controller 222 may receive an input from a program stored in the memory of the controller 222 or from another controller and uses a look up table stored in the memory of the controller 222 to correlate the input to a particular current that when provided to the heat source 1200 generates (for example, radiates) a particular amount of heat from the heat source 1200. In different alternative embodiments, the controller 222 receives an input as described above and uses a look up table stored in the memory of the controller 222 to correlate the input to a particular chemical mixture that when mixed together generates a particular amount of heat from the heat source 1200. The controller 222 may provide the particular current to the heat source 1200 or control the mixing component in the heat source 1200 to generate the amount of heat that correlates with the input.

The following examples illustrate example methods and devices described herein.

Example 1 a dental handpiece comprising a power source, a controller electrically connected to the power source, a vibration generator configured to generate vibrations by rotating an imbalanced mass, the vibration generator having an electric motor electrically connected to the controller, a linear electromagnetic actuator electrically connected to the controller, a magnet, a container configured to hold a material and having a piston, a vibration transmission element configured to transmit vibrations caused by rotation of the imbalanced mass to the container, and a tip, wherein the linear electromagnetic actuator is configured to move the piston of the container to dispense the material through the tip while the container is vibrated by the vibration transmission element.

Example 2 the dental handpiece of example 1, wherein the linear electromagnetic actuator comprises a moving magnet actuator, wherein the moving magnet actuator includes at least two coils that are configured to generate a magnetic field gradient to apply a force that moves the magnet, and wherein the magnet is configured to move the piston.

Example 3 the dental handpiece of any of examples 1 and 2, wherein the linear electromagnetic actuator comprises a voice coil actuator, wherein the voice coil actuator includes a mover and a stator, wherein the mover includes a coil in mechanical communication with the piston, wherein the stator includes the magnet, and wherein the coil is configured to generate a magnetic field that repels the coil from the magnet to apply a force that moves the piston.

Example 4 the dental handpiece of any of examples 1-3, wherein the linear electromagnetic actuator comprises an inverted voice coil actuator, wherein the inverted voice coil actuator includes a mover and a stator, wherein the mover includes a magnet in mechanical communication with the piston, wherein the stator includes a coil, and wherein the coil is configured to generate a magnetic field that repels the magnet from the coil to apply a force that moves the piston.

Example 5 the dental handpiece of any of examples 1-4, further comprising an imbalanced flywheel rotationally coupled to the electric motor, the imbalanced flywheel comprising the imbalanced mass.

Example 6 the dental handpiece of example 5, wherein the vibration generator further comprises a second electric motor electrically connected to the controller, and a second imbalanced flywheel rotationally coupled to the second electric motor, wherein the vibration transmission element is configured to transmit vibrations caused by rotation of the imbalanced flywheel and the second imbalanced flywheel to the material of the container.

Example 7 the dental handpiece of example 6, wherein the vibration transmission element is further configured to reduce a viscosity of the material with the vibrations caused by the rotation of the imbalanced flywheel and the second imbalanced flywheel.

Example 8 the dental handpiece of any of examples 1-7, wherein the electric motor is an imbalanced electric motor, and wherein the electric motor includes the imbalanced mass.

Example 9 the dental handpiece of any of examples 1-8, further comprising a material identification component that is configured to provide a signal to the controller that is indicative of a type of the material, wherein the controller is further configured to identify the type of the material based on the signal from the material identification component, determine whether the material is suitable for pre-mixing based on the identification of the type of the material, and responsive to determining that the material is suitable for pre-mixing, control the electric motor to pre-mix the material prior to dispensing the material from the container.

Example 10 the dental handpiece of any of examples 1-9, further comprising a heat source that is configured to radiate heat toward the material in the container, wherein the controller is further configured to receive an input that is indicative of an amount of heat to be radiated towards the container and control the heat source to provide the amount of heat based on the input.

Example 11 a method for dispensing a material within a container of a dental handpiece. The method comprising receiving an input that indicates that an amount of the material is to be dispensed from the container of the dental handpiece, rotating an electric motor to rotate an imbalanced mass to vibrate a vibration transmission element that vibrates the material in the container, and dispensing the amount of the material from the container with a piston based on the input.

Example 12 the method of example 11, wherein receiving the input that indicates that the amount of the material is to be dispensed from the container comprises receiving the input by at least one of a controller or a squeeze handle.

Example 13 the method of any of examples 11 and 12, wherein rotating the imbalanced mass to vibrate the vibration transmission element that vibrates the material in the container comprises receiving a second input, and responsive to receiving the second input, rotating the electric motor to rotate the imbalanced mass to vibrate the vibration transmission element that vibrates the material in the container.

Example 14 the method of example 13, wherein the input that indicates the amount of the material to be dispensed from the container and the second input are the same input.

Example 15 the method of any of examples 11-14, wherein dispensing the amount of the material from the container with the piston based on the input comprises controlling, by a controller, at least two coils to generate a magnetic field gradient that applies a force on a magnet configured to move the piston.

Example 16 the method of any of examples 11-15, wherein dispensing the amount of the material from the container with the piston based on the input comprises controlling, by a controller, a coil in mechanical communication with the piston to generate a magnetic field that applies a force on the coil that moves the piston away from a magnet.

Example 17 the method of any of examples 11-16, wherein dispensing the amount of the material from the container with the piston based on the input comprises controlling, by a controller, a coil to generate a magnetic field that applies a force on a magnet in mechanical communication with the piston that moves the piston away from the coil.

Example 18 the method of any of examples 11-17, wherein dispensing the amount of the material from the container with the piston based on the input comprises receiving, by a squeeze handle, a force that moves a pushrod configured to move the piston.

Example 19 the method of any of examples 11-18, wherein the electric motor is an imbalanced electric motor, and wherein the electric motor includes the imbalanced mass.

Example 20 the method of any of examples 11-19, further comprising identifying, by a controller, a type of the material based on a signal from a material identification component, determine, by the controller, whether the material is suitable for pre-mixing based on the identification of the type of the material, and responsive to determining that the material is suitable for pre-mixing, controlling, by the controller, the electric motor to pre-mix the material prior to dispensing the material from the container.

Example 21 the method of any of claims 11-20, further comprising receiving, by a controller, an input indicative of an amount of heat to be radiated towards the container, and controlling, by the controller, a heat source to provide the amount of heat based on the input.

Example 22 a dental handpiece comprising a squeeze handle mechanically linked to a pushrod, a vibration generator configured to generate vibrations by rotating an imbalanced mass, the vibration generator having an electric motor, a container configured to hold a material and having a piston, a vibration transmission element configured to transmit vibrations caused by rotation of the imbalanced mass to the material of the container, and a tip, wherein the squeeze handle and the pushrod are configured to move the piston of the container to dispense the material through the tip while the container is vibrated.

Example 23 the dental handpiece of example 22, further comprising a housing, and a spring positioned between the squeeze handle and the housing, wherein the spring is configured to maintain the squeeze handle in a steady state position when there is no force applied to the squeeze handle.

Example 24 the dental handpiece of examples 22 and 23, further comprising an imbalanced flywheel rotationally coupled to the electric motor, the imbalanced flywheel comprising the imbalanced mass.

Example 25 the dental handpiece of any of examples 22-24, wherein the vibration generator further comprises a second electric motor, and a second imbalanced flywheel rotationally coupled to the second electric motor, wherein the vibration transmission element is configured to transmit vibrations caused by rotation of the imbalanced flywheel and the second imbalanced flywheel to the material of the container.

Example 26 the dental handpiece of any of examples 22-25, wherein the electric motor is an imbalanced electric motor, and wherein the electric motor includes the imbalanced mass.

Example 27 the dental handpiece of any of examples 22-26, further comprising a controller and a material identification component that is configured to provide a signal to the controller that is indicative of a type of the material, wherein the controller is configured to identify the type of the material based on the signal from the material identification component, determine whether the material is suitable for pre-mixing based on the identification of the type of the material, and responsive to determining that the material is suitable for pre-mixing, control the electric motor to pre-mix the material prior to dispensing the material from the container.

Example 28 the dental handpiece of any of examples 22-27, further comprising a controller and a heat source that is configured to radiate heat toward the material in the container, wherein the controller is configured to receive an input that is indicative of an amount of heat to be radiated towards the container and control the heat source to provide the amount of heat based on the input.

Example 29 a dental handpiece comprising a power source, a controller electrically connected to the power source, a vibration generator having a plurality of stator coils that are configured to generate a rotating magnetic field, and a member that is configured to vibrate in response to the rotating magnetic field, a linear electromagnetic actuator electrically connected to the controller, a magnet, a container configured to hold a material and having a piston, wherein the container is configured to receive vibrations transmitted by the member, and a tip, wherein the linear electromagnetic actuator is configured to move the piston of the container to dispense the material through the tip while the container receives the vibrations transmitted by the member.

Example 30 the dental handpiece of example 29, wherein the member is conductive.

Example 31 the dental handpiece of examples 29 and 30, wherein the member is magnetic.

Example 32 the dental handpiece of any of examples 29-31, wherein the linear electromagnetic actuator comprises a moving magnet actuator, wherein the moving magnet actuator includes at least two coils that are configured to generate a magnetic field gradient to apply a force that moves the magnet, and wherein the magnet is configured to move the piston.

Example 33 the dental handpiece of any of examples 29-32, wherein the linear electromagnetic actuator comprises a voice coil actuator, wherein the voice coil actuator includes a mover and a stator, wherein the mover includes a coil in mechanical communication with the piston, wherein the stator includes the magnet, and wherein the coil is configured to generate a magnetic field that repels the coil from the magnet to apply a force that moves the piston.

Example 34 the dental handpiece of any of examples 29-33, wherein the linear electromagnetic actuator comprises an inverted voice coil actuator, wherein the inverted voice coil actuator includes a mover and a stator, wherein the mover includes a magnet in mechanical communication with the piston, wherein the stator includes a coil, and wherein the coil is configured to generate a magnetic field that repels the magnet from the coil to apply a force that moves the piston.

Example 35 the dental handpiece of any of examples 29-34, further comprising a material identification component that is configured to provide a signal to the controller that is indicative of a type of the material, wherein the controller is further configured to identify the type of the material based on the signal from the material identification component, determine whether the material is suitable for pre-mixing based on the identification of the type of the material, and responsive to determining that the material is suitable for pre-mixing, control the electric motor to pre-mix the material prior to dispensing the material from the container.

Example 36 the dental handpiece of any of examples 29-35, further comprising a heat source that is configured to radiate heat toward the material in the container, wherein the controller is further configured to receive an input that is indicative of an amount of heat to be radiated towards the container and control the heat source to provide the amount of heat based on the input.

Example 37 the method of any of examples 11-21, wherein the imbalanced mass is part of an imbalanced flywheel rotationally coupled to the electric motor.

Thus, embodiments of the invention provide, among other things, alternative solutions for generating vibrations for a dental handpiece that do not require currently known pneumatic devices or piezo devices. Various features and advantages of the invention are set forth in the following claims.

What is claimed is:
1. A dental handpiece comprising:
a power source;
a controller electrically connected to the power source;
a vibration generator configured to generate vibrations by rotating an imbalanced mass, the vibration generator having an electric motor electrically connected to the controller,
a linear electromagnetic actuator electrically connected to the controller;
a magnet;
a container configured to hold a material and having a piston;
a vibration transmission element configured to transmit vibrations caused by rotation of the imbalanced mass to the container; and
a tip,
wherein the linear electromagnetic actuator is configured to move the piston of the container to dispense the material through the tip while the container is vibrated by the vibration transmission element.

2. The dental handpiece of claim 1, wherein the linear electromagnetic actuator comprises a moving magnet actuator, wherein the moving magnet actuator includes at least two coils that are configured to generate a magnetic field gradient to apply a force that moves the magnet, and wherein the magnet is configured to move the piston.

3. The dental handpiece of claim 1, wherein the linear electromagnetic actuator comprises a voice coil actuator, wherein the voice coil actuator includes a mover and a stator, wherein the mover includes a coil in mechanical communication with the piston, wherein the stator includes the magnet, and wherein the coil is configured to generate a magnetic field that repels the coil from the magnet to apply a force that moves the piston.

4. The dental handpiece of claim 1, wherein the linear electromagnetic actuator comprises an inverted voice coil actuator, wherein the inverted voice coil actuator includes a mover and a stator, wherein the mover includes the magnet in mechanical communication with the piston, wherein the stator includes a coil, and wherein the coil is configured to generate a magnetic field that repels the magnet from the coil to apply a force that moves the piston.

5. The dental handpiece of claim 1, further comprising an imbalanced flywheel rotationally coupled to the electric motor, the imbalanced flywheel comprising the imbalanced mass.

6. The dental handpiece of claim 5, wherein the vibration generator further comprises:
a second electric motor electrically connected to the controller, and
a second imbalanced flywheel rotationally coupled to the second electric motor,
wherein the vibration transmission element is configured to transmit vibrations caused by rotation of the imbalanced flywheel and the second imbalanced flywheel to the material of the container.

7. The dental handpiece of claim 6, wherein the vibration transmission element is further configured to reduce a viscosity of the material with the vibrations caused by the rotation of the imbalanced flywheel and the second imbalanced flywheel.

8. The dental handpiece of claim 1, wherein the electric motor is an imbalanced electric motor, and wherein the electric motor includes the imbalanced mass.

9. The dental handpiece of claim 1, further comprising a material identification component that is configured to provide a signal to the controller that is indicative of a type of the material, wherein the controller is further configured to identify the type of the material based on the signal from the material identification component, determine whether the material is suitable for pre-mixing based on the identification of the type of the material, and responsive to determining that the material is suitable for pre-mixing, control the electric motor to pre-mix the material prior to dispensing the material from the container.

10. The dental handpiece of claim 1, further comprising a heat source that is configured to radiate heat toward the material in the container, wherein the controller is further configured to receive an input that is indicative of an amount of heat to be radiated towards the container and control the heat source to provide the amount of heat based on the input.

11. A method for dispensing a material within a container of a dental handpiece, the method comprising:
receiving an input that indicates that an amount of the material is to be dispensed from the container of the dental handpiece;
rotating an electric motor to rotate an imbalanced mass to vibrate a vibration transmission element that vibrates the material in the container, wherein the imbalanced mass is non-eccentrically mounted to the electric motor at a center point of the imbalanced mass; and
dispensing the amount of the material from the container with a piston based on the input,
wherein dispensing the amount of the material from the container with the piston based on the input comprises controlling, by a controller, at least two coils to generate a magnetic field gradient that applies a force on a magnet configured to move the piston.

12. The method of claim 11, wherein receiving the input that indicates that the amount of the material is to be dispensed from the container comprises receiving the input by at least one of the controller or a squeeze handle.

13. The method of claim 11, wherein rotating the imbalanced mass to vibrate the vibration transmission element that vibrates the material in the container comprises:
receiving a second input; and
responsive to receiving the second input, rotating the electric motor to rotate the imbalanced mass to vibrate the vibration transmission element that vibrates the material in the container.

14. The method of claim 13, wherein the input that indicates the amount of the material to be dispensed from the container and the second input are the same input.

15. The method of claim 11, wherein the electric motor is an imbalanced electric motor, and wherein the electric motor includes the imbalanced mass.

16. A method for dispensing a material within a container of a dental handpiece, the method comprising:
receiving an input that indicates that an amount of the material is to be dispensed from the container of the dental handpiece;
rotating an electric motor to rotate an imbalanced mass to vibrate a vibration transmission element that vibrates the material in the container, wherein the imbalanced mass is non-eccentrically mounted to the electric motor at a center point of the imbalanced mass; and
dispensing the amount of the material from the container with a piston based on the input,
wherein dispensing the amount of the material from the container with the piston based on the input comprises controlling, by a controller, a coil in mechanical communication with the piston to generate a magnetic field that applies a force on the coil that moves the piston away from a magnet.

17. A method for dispensing a material within a container of a dental handpiece, the method comprising:
receiving an input that indicates that an amount of the material is to be dispensed from the container of the dental handpiece;
rotating an electric motor to rotate an imbalanced mass to vibrate a vibration transmission element that vibrates the material in the container, wherein the imbalanced mass is non-eccentrically mounted to the electric motor at a center point of the imbalanced mass; and
dispensing the amount of the material from the container with a piston based on the input,
wherein dispensing the amount of the material from the container with the piston based on the input comprises controlling, by a controller, a coil to generate a magnetic field that applies a force on a magnet in mechanical communication with the piston that moves the piston away from the coil.

18. A method for dispensing a material within a container of a dental handpiece, the method comprising:
receiving an input that indicates that an amount of the material is to be dispensed from the container of the dental handpiece;
rotating an electric motor to rotate an imbalanced mass to vibrate a vibration transmission element that vibrates the material in the container, wherein the imbalanced mass is non-eccentrically mounted to the electric motor at a center point of the imbalanced mass;
dispensing the amount of the material from the container with a piston based on the input,
identifying, by a controller, a type of the material based on a signal from a material identification component;
determining, by the controller, whether the material is suitable for pre-mixing based on the identification of the type of the material; and
responsive to determining that the material is suitable for pre-mixing, controlling, by the controller, the electric motor to pre-mix the material prior to dispensing the material from the container.

19. The method of claim 18, wherein dispensing the amount of the material from the container with the piston based on the input comprises receiving, by a squeeze handle, a force that moves a pushrod configured to move the piston.

20. A method for dispensing a material within a container of a dental handpiece, the method comprising:
receiving an input that indicates that an amount of the material is to be dispensed from the container of the dental handpiece;
rotating an electric motor to rotate an imbalanced mass to vibrate a vibration transmission element that vibrates the material in the container, wherein the imbalanced mass is non-eccentrically mounted to the electric motor at a center point of the imbalanced mass;
dispensing the amount of the material from the container with a piston based on the input,
receiving, by a controller, an input indicative of an amount of heat to be radiated towards the container; and
controlling, by the controller, a heat source to provide the amount of heat based on the input.

21. The method of claim 20, wherein dispensing the amount of the material from the container with the piston based on the input comprises receiving, by a squeeze handle, a force that moves a pushrod configured to move the piston.

22. A dental handpiece comprising:
a power source;
a controller electrically connected to the power source;

a vibration generator having
  a plurality of stator coils that are configured to generate a rotating magnetic field, and
  a member that is configured to vibrate in response to the rotating magnetic field;
a linear electromagnetic actuator electrically connected to the controller;
a magnet;
a container configured to hold a material and having a piston, wherein the container is configured to receive vibrations transmitted by the member, and
a tip,
wherein the linear electromagnetic actuator is configured to move the piston of the container to dispense the material through the tip while the container receives the vibrations transmitted by the member.

23. The dental handpiece of claim 22, wherein the member is conductive.

24. The dental handpiece of claim 22, wherein the member is magnetic.

* * * * *